(12) United States Patent
Vale et al.

(10) Patent No.: US 7,252,950 B1
(45) Date of Patent: Aug. 7, 2007

(54) ASSAYS FOR DETECTING MODULATORS OF CYTOSKELETAL FUNCTION

(75) Inventors: Ronald Vale, Tiburon, CA (US); Daniel Pierce, Hayward, CA (US); James Spudich, Palo Alto, CA (US)

(73) Assignees: The Regents of the University of California, Oakland, CA (US); The Board of Trustees of The Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 10/031,819

(22) PCT Filed: Sep. 3, 1998

(86) PCT No.: PCT/US98/18368

§ 371 (c)(1),
(2), (4) Date: Aug. 12, 2002

(87) PCT Pub. No.: WO99/11814

PCT Pub. Date: Mar. 11, 1999

Related U.S. Application Data

(60) Continuation-in-part of application No. 09/724,609, filed on Nov. 28, 2000, now Pat. No. 6,489,134, which is a division of application No. 09/226,772, filed on Jan. 6, 1999, now Pat. No. 6,207,403.

(60) Provisional application No. 60/070,772, filed on Jan. 8, 1998, provisional application No. 60/057,895, filed on Sep. 4, 1997.

(51) Int. Cl.
  *G01N 33/53* (2006.01)
  *C12N 9/14* (2006.01)
  *C12N 9/16* (2006.01)

(52) U.S. Cl. .................. 435/7.1; 435/195; 435/196; 435/DIG. 2

(58) Field of Classification Search .................. 435/30, 435/7.1, 195, 196, DIG. 2
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 4,391,904 A | 7/1983 | Litman et al. | |
| 4,469,863 A | 9/1984 | Ts'o et al. | |
| 5,010,175 A | 4/1991 | Rutter et al. | |
| 5,034,506 A | 7/1991 | Summerton et al. | |
| 5,143,854 A | 9/1992 | Pirrung et al. | |
| 5,216,141 A | 6/1993 | Benner | |
| 5,235,033 A | 8/1993 | Summerton et al. | |
| 5,288,514 A | 2/1994 | Ellman | |
| 5,386,023 A | 1/1995 | Sanghvi et al. | |
| 5,506,337 A | 4/1996 | Summerton et al. | |
| 5,519,134 A | 5/1996 | Acevedo et al. | |
| 5,525,735 A | 6/1996 | Gallop et al. | |
| 5,527,773 A | 6/1996 | Steinert et al. ............... 514/12 |
| 5,539,083 A | 7/1996 | Cook et al. | |
| 5,541,061 A | 7/1996 | Fodor et al. | |
| 5,549,974 A | 8/1996 | Holmes | |
| 5,559,410 A | 9/1996 | Papazian et al. | |
| 5,569,588 A | 10/1996 | Ashby et al. | |
| 5,576,220 A | 11/1996 | Hudson et al. | |
| 5,585,639 A | 12/1996 | Dorsel et al. | |
| 5,593,853 A | 1/1997 | Chen et al. | |
| 5,602,240 A | 2/1997 | De Mesmaeker et al. | |
| 5,637,684 A | 6/1997 | Cook et al. | |
| 5,644,048 A | 7/1997 | Yau | |
| 6,207,403 B1 * | 3/2001 | Goldstein et al. ............. 435/21 |

FOREIGN PATENT DOCUMENTS

| | | |
|---|---|---|
| WO | WO 90/15070 | 12/1990 |
| WO | WO 91/19735 | 12/1991 |
| WO | WO 92/00091 | 1/1992 |
| WO | WO 92/10092 | 6/1992 |
| WO | WO 93/09668 | 5/1993 |
| WO | WO 93/11231 | 6/1993 |
| WO | WO 93/20242 | 10/1993 |

(Continued)

OTHER PUBLICATIONS

Sakowicz et al., (Apr. 10, 1998) Science vol. 280, pp. 292-295.*

(Continued)

*Primary Examiner*—Mark L. Shibuya
(74) *Attorney, Agent, or Firm*—Medlen & Carroll, LLP

(57) ABSTRACT

Described herein are methods of identifying compounds which modulate the activity of the cytoskeletal system. The methods are rapid, convenient and sensitive. Preferably, the method is used to identify lead compounds that can be used as therapeutics, diagnostics and agricultural agents. Generally, test compounds are added to two cytoskeletal components which bind to one another, to determine whether the binding is affected by the test compound. Wherein the binding is affected, a compound which modulates the cytoskeletal system is identified.

7 Claims, 2 Drawing Sheets

FOREIGN PATENT DOCUMENTS

| WO | WO94/08041 | * | 4/1994 |
|---|---|---|---|
| WO | WO 96/30766 | | 10/1996 |
| WO | WO 97/00271 | | 1/1997 |

OTHER PUBLICATIONS

Stewart et al., (Jun. 1993) Proc. Natl. Acad. Sci. USA, vol. 90, pp. 5209-5213.*
Hopkins et al., (Feb. 2000), Inhibitors of Kinesin Activity from Structure-Based Computer Screening, Biochemistry, vol. 39, pp. 2805-2814.*
Makino et al., Biochemical and Biophysical Communications (1996), vol. 220, pp. 1049-1054.*
Alberts et al., 1994, in *Molecular Biology of the Cell*, 3rd ed., Garland Publishing, Inc., New York, pp. 788-858.
Goldstein (1993) "With Apologies to Scheherazade: Tails of 1001 Kinesin Motors," Ann. Rev. Genetics 27:319-351.
Mooseker and Cheney (1995) "Unconventional Myosins,"Annu. Rev. Cell Biol. 11:663-675.
Turner et al.(1996) "Kinesin Movement on Glutaraldehyde-Fixed Microtubules," Anal. Biochem. 242(1):20-25.
Gittes et al. (1996) "Directional Loading of the Kinesin Motor Molecule as it Buckles a Microtubule," Biophys. J. 70(1):418-29.
Shirakawa et al., (1995) "The Mode of ATP-Dependent Microtubule-Kinesin Sliding in the Auxotonic Condition," J. Exp. Biol. 198:1809-15.
Winkelmann et al. (1995) "Flexibility of Mysoin Attachment to Surfaces Influences F-Actin Motion," Biophys. J. 68:2444-53.
Winkelmann et al. (1995) "Motility Assays Using Myosin Attached to Surfaces through Specific Binding to Monoclonal Antibodies," Biophys J. 68:72S.
Kuby (1992) *Immunology*, W.H. Freeman and Company, New York, pp. 122-124.
Stryer (1978) "Fluorescence Energy Transfer as a Spectrocopic Ruler," Ann. Rev. Biochem. 47:819-846.
Taylor et al. (1981) "Detection of Actin Assembly by Fluorescence Energy Transfer," J. Cell Biol. 89:362-367.
Yamamoto et al. (1982) "Mechanism of Interaction of *Dictyostelium* Severin with Actin Filaments," J. Cell Biol. 95:711-719.
Gupta et al. (1998) "Optical Amplification of Ligand-Receptor Binding Using Liquid Crystals," Science 279:2077-2080.
Chien et al. (1991) "The two-hybrid system: A method to identify and clone genes for proteins that interact with a protein of interest," Proc Natl. Acad. Sci. USA 88:9578-9582.
Fields and Song (1989) "A novel genetic system to detect protein-protein interactions," Nature 340:245-246.
Chevray and Nathans (1992) "Protein interaction cloning in yeast: Identification of mammalian proteins that react with the leucine zipper of Jun," Proc. Natl. Acad. Sci. USA 89:5789-5793.
Fodor et al. (1991) "Light-Directed, Spatially Addressable Parallel Chemical Synthesis," Science 251:767-773.
Burridge et al. (1996) "Focal Adhesions, Contractility, and Signaling," Ann. Rev. Cell Dev. Biol. 12:463-519.
Cuatrecasas (1970) "Protein Purification by Affinity Chromatography," J. Biol. Chem. 245:3059.
Collioud et al. (1993) "Oriented and Covalent Immobilization of Target Molecules to Solid Supports: Synthesis and Application of a Light-Activatable and Thiol-Reactive Cross-Linking Reagent," Bioconjugate Chem. 4:528-536.
Schuhmann et al. (1991) "Immobilization of Enzymes on Langmuir-Blodgett Films via a Membrane-Bound Receptor. Possible Applications for Amperometric Biosensors," Adv. Mater. 3:388-391.
Lu et al. (1995) "Oriented Immobilization of Fab' Fragments on Silica Surfaces," Anal. Chem. 67:83-87.
Iwane et al. (1997) "Myosin Subfragment-1 Is Fully Equipped with Factors Essential for Motor Function," Biophys. Biochem. Res. Comm. 230:76-80.
Ng et al. (1995) "Engineering Protein—Lipid Interactions: Targeting of Histidine-Tagged Proteins to Metal-Chelating Lipid Monolayers," Langmuir 11 :4048-4055.
Schmitt et al. (1996) Specific Proteins Docking to Chelator Lipid Monolayers Monitored by FT-IR Spectrometry at the Air-Water Interface, Angew. Chem. Int. Ed. Engl. 35:317-320.
Frey et al. (1996) "Two-dimensional protein crystallization via metal-ion coordination by naturally occuring surface histidines," Proc. Natl. Acad. Sci. USA 93:4937-4941.
Kubalek et al. (1994) "Two-Dimensional Crystallization of Histidine-Tagged, HIV-1 Reverse Transcriptase Promoted by a Novel Nickel-Chelating Lipid," J. Struct. Biol. 113:117-123.
Sigal et al. (1996) "A Self-Assembled Monolayer for the Binding and Study of Histidine-Tagged Proteins by Surface Plasmon Resonance," Anal. Chem. 68:490-497.
Beaucage et al. (1993) "The Functionalization of Oligonucleotides Via Phosphoramidite Derivatives," Tetrahedron 49:1925.
Letsinger (1970) "Phosphoramidate Analogs of Oligonucleotides," J. Org. Chem. 35:3800.
Sprinzl et al. (1977) "Enzymatic Incorporation of ATP and CTP Analogues into the 3' End of tRNA," Eur. J. Biochem. 81:579.
Letsinger et al. (1986) "Effects of pendant groups at phosphorous on binding properties of d-ApA analogues," Nucl. Acids Res. 14:3487.
Sawai et al. (1984) "Synthesis and Properties of Oligoadenylic Acids Containing 2'-5' Phosphoramide Linkage," Chem. Lett. 805.
Letsinger et al. (1988) "Cationic Oligonucelotides," J. Am. Chem. Soc. 110:4470.
Pauwels et al. (1986) "Biological Activity of New 2-5A Analogues," Chemica Scripta 26:141-145.
Mag et al. (1991) "Synthesis and selective cleavage of an oligodeoxynucleotide containing a bridged internucletotide 5'-phosphorothiote linkage," Nucl. Acids. Res. 19:1437.
Brill et al. (1989) "Synthesis of Oligodeoxynucelotide Phosphorodithiotes via Thioamidites," J. Am. Chem. Soc. 111:2321.
Egholm (1992) "Peptide Nucleic Acids (PNA). Oligonucleotide Analogues with an Achiral Peptide Backbone," J. Am. Chem. Soc. 114:1895.
Meier et al. (1992) "Peptide Nucleic Acids (PNAs)—Unusual Properties of Nonionic Oligonucelotides Analogues," Angew. Chem. Int. Ed. Engl. 31:1008.
Egholm et al. (1992) "PNA hybridized to complementary oligonucleotides obeying the Watson-Crick hydrogen-bonding rules," Nature 365:566.
Carlsson et al. (1996) "Screening for genetic mutations," Nature 380:207.
Dempcy et al. (1995) "Synthesis of a thymidyl pentamer of deoxyribonucleic guanidine and binding studies with DNA homopolynucleotides," Proc. Natl. Acad. Sci. USA 92:6097.
Kiedrowski et al. "Parabolic Growth of a Self-Replicating Hexadeoxynucleotide Bearing a 3'-5'-Phosphoamidate Linkage," (1991) Angew Chem. Intl. Ed. English 30:423.
Jung et al. (1994) "Hybridization of Alternating Cationic/Anionic Oligonucleotides to RNA Segments," Nucleosides and Nucleotides 13:1597.
Carbohydrate Modifications in Antisense Research, Chapters 2 and 3 in *ACS Symposium Series 580*, Sanghvi and Cook, ed., 1994.
De Mesmaeker et al. (1994) "Comparison of Rigid and Flexible Backbones in Antisense Oligonucleotides," Bioorganic and Medicinal Chem. Lett. 4:395.
Gao and Jeffs (1994) "Unusual conformation of a 3'-thioformacetal linkage in a DNA duplex," J. Biomolecular NMR 4:17.
Horn et al. (1996) "Oligonucleotides with Alternating Anionic and Cationic Phosphoramidate Linkages: Synthesis and Hybridizatiion of Stereo-uniform Isomers," Tetrahedron Lett. 37:743.
Carbohydrate Modifications in Antisense Research, Chapters 6 and 7 in *ACS Symposium Series 580*, Sanghvi and Cook, eds., 1994.
Jenkins et al. (1995) "The Biosynthesis of Carbocyclic Nucleotides," Chem. Soc. Rev., pp. 169-176.
Rawls "Optimistic About Antisense," C&E, Jun. 2, 1997, pp. 35-39.
Gallop et al. (1994) "Applications of Combinatorial Technologies to Drug Delivery. I. Background and Peptide Combinatorial Libraries," J. Med. Chem. 37(9):1233-1251.
*Combinatorial Chemistry and Molecular Diversity in Drug Discovery*, John Wiley & Sons, Inc., NY, Gordon and Kerwin, ed., 1998.

Furka (1991) "General method for rapid synthesis of multicomponent peptide mixtures," Int. J. Pept. Prot. Res.37:487-493.

Houghten et al. (1991) "Generation and use of synthetic peptide combinatorial libraries for basic research and drug discovery," Nature 354:84-88.

DeWitt et al. (1993) "'Diversomers': An approach to nonpeptide, nonoligomeric chemical diversity," Proc. Natl. Acad. Sci. USA 90:6909-6913.

Hagihara et al. (1992) "Vinylogous Polypeptides: An Alternative Peptide Backbones," J. Amer. Chem. Soc. 114:6568.

Hirschmann et al. (1992) "Nonpeptidal Peptidomimetics with a β-D-Glucose Scaffolding. A Partial Somatostatin Agonist Bearing a Close Structural Relationship to a Potent, Selective Substance P Antagonist," J. Amer. Chem. Soc. 114:9217-9218.

Chen et al. (1994) "'Analogues" Organic Synthesis of Small-Compound Libraries: Validation of Combinatorial Chemistry in Small-Molecule Synthesis, 'J. Amer. Chem. Soc. 116:2661.

Cho et al. (1993) "An Unnatural Biopolymer," Science 261:1303.

Campbell et al. (1994) "Phosphate Ester Synthesis Using a Modified Mitsunobu Condensation," J. Org. Chem. 59:658.

Gordon et al. (1994) "Applications of Combinatorial Technologies to a Drug Discovery. 2. Combinatorial Prgamoc Synthesis, Library Screening Strategies, and Future Directions." J. Med. Chem. 37:1386.

Vaughan et al. (1996) "Human Antibodies with Sub-nanomolar Affinities Isolated from a Large Non-immunized Phage Display Library," Nature Biotechnology 14(3):309-314.

Liang et al. (1996) "Parallel Synthesis and Screening of a Solid Phase Carbohydrate Library," Science 274:1520-1522.

Baum (1993) "Solid-phase synthesis of benzodiazepines," C&EN, Jan. 18, pp. 33-34.

Köhler and Milstein (1975) "Continuous cultures of fused cells secreting antibody of predefined specificity," Nature 256:495-497.

Huse et al. (1989) "Generation of a Large Combinatorial Library of the Immunoglobulin Repertoire in Phage Lambda," Science 246:1275-1281.

Ward et al. (1989) "Binding activities of a repertoire of single immunoglobulin variable domains secreted from *Escherichia coli*," Nature 341:544-546.

Köhler and Milstein (1976) "Derivation of specific antibody-producing tissue culture and tumor lines cell fusion," Eur. J. Immunol. 6:511-519.

Harlow and Lane (1988) *Antibodies: A Laboratory Manual*, Cold Spring Harbor Press, NY, pp. 570-573.

Pierce et al. (1997) "Imaging individual green fluorescent proteins," Nature 388:338.

Chandra et al. (1993) "Structural and Functional Domains of the *Drosophila* ncd Microtubule Motor Protein," J. Biol. Chem. 268:9005-9013.

Woehlke et al. (1997) "Microtubule Interaction Site of the Kinesin Motor," Cell 90:207-216.

Harada et al. (1990) "Mechanochemical Coupling in Actomyosin Energy Transduction Studies by in Vitro Movement Assay," J. Mol. Biol. 216:49-68.

Hyman (1991) "Preparation of marked microtubules for the assay of the polarity of microtubule-based motors by fluorescence," J. Cell. Sci. Suppl 14:125-127.

Gibbons and Fronk (1979) "A Latent Adeosine Triphosphatase Form of Dynein 1 from Sea Urchin Sperm Flagells," J. Biol. Chem. 254:187-196.

Valc et al. (1996) "Direct observation of single kinesin molecules moving along microtubules," Nature 380:451-453.

Funatsu et al. (1995) "Imaging of single fluroescent molecules and individual ATP turnovers by single myosin molecules in aqueous solution," Nature 374:555-559.

Geladopoulos et al. (1991) "A Malachite Green Colotimetric Assay for Protein Phosphate Activity," Anal. Biochem. 192:112-116.

Hackney (1994) "The Rate-limiting Step in Microtubule-stimulated ATP Hydrolysis by Dimeric Kinesin Head Domains Occurs While Bound to the Microtubule," J. Biol. Chem. 2690:16508-16511.

Ma et al. (1996) "Colocalization of cell division proteins FtsZ and FtsA to cytoskeletal structures in living *Escherichia coli* cells by using green fluorescent protein," Proc. Soc. Natl. Acad. Sci. USA 93:12998-13003.

Ludin et al. (1996) "Application of novel vectors for GFP-tagging of proteins to study microtubule-associated proteins," Gene 173:107-111.

Endow et al. (1996) "Centrosome and spindle function of the *Drosophilia* Ned micotubule motor visualized in live embryos using Ned-GFP fusion proteins," J. Cell Sci. 109:2429-2442.

Olson et al. (1995) "Analysis of MAP 4 Function in Living Cells Using Green Fluorescent Protein (GFP) Chimeras," J. Cell. Biol. 130:639-650.

Gerisch et al. (1995) "Chemoattractant-controlled accumulation of coronin at the leading edge of Dictostelium cells monitored using a green fluorescent protein-coronin fusion protein," Curr. Biol. 5:1280-1285.

Broach et al. (1996) "High-throughput screening for drug discovery," Nature 384, Suppl. 7:14-16.

Duncan et al., "Cucurbitacin E-induced disruption of the actin and vimentin cytoskeleton in prostate carcinoma cells," *Biochem Pharmacol*, 52:1553-1560, 1996.

Howard et al., "Movement of microtubules by single kinesin molecules," *Nature*, 342:154-158, 1989.

Orlando et al., "Arginine-glycine-aspartic acid binding leading to molecular stabilization between integrin $\alpha_v\beta_3$ and its ligand," *J Biol Chem*, 266:19543-19550, 1991.

Romberg et al., "Chemomechanical cycle of kinesin differs from that of myosin," *Nature*, 361:168-170, 1993.

Senter et al., "Interaction of dystrophin with cytoskeletal proteins: binding to talin and actin," *Biochem Biophys Res Comm*, 192:899-904, 1993.

\* cited by examiner

CONSTRUCTS

K560

NK-1

NK-2

NK-3

K560-GFP

Ncd-GFP

NK-1-GFP

ASSAYS FOR DETECTING MODULATORS OF CYTOSKELETAL FUNCTION

CROSS-REFERENCE TO RELATED APPLICATIONS

This application is a U.S. national entry of International Application No. PCT/US98/18368, filed on Sep. 3, 1998, which claims priority to U.S. Provisional Application No. 60/057,895, filed on Sep. 4, 1997 which is incorporated herein by reference in its entirety for all purposes. This application is also a Continuation-in-Part of U.S. application Ser. No. 09/724,609, filed on Nov. 28, 2000, now U.S. Pat. No. 6,489,134, which is a Divisional of U.S. application Ser. No. 09/226,772, filed Jan. 6, 1999, now U.S. Pat. No. 6,207,403, which claims priority to U.S. Provisional Application No. 60/070,772, filed on Jan. 8, 1998.

STATEMENT AS TO RIGHTS TO INVENTIONS MADE UNDER FEDERALLY SPONSORED RESEARCH AND DEVELOPMENT

This work was supported in part by Grant Numbers gm35252 gm38499, gm332289, gm40509, and gm46551 from the National Institutes of Health. The Government of the United States of America may have rights in this invention.

FIELD OF THE INVENTION

This invention relates to assays for identifying compounds that modulate the activity of a cytoskeletal system (e.g. an actin/myosin system, a tubulin system, etc.).

BACKGROUND OF THE INVENTION

The cytoskeleton constitutes a large family of proteins that are involved in many critical processes of biology, such as chromosome and cell division, cell motility and intracellular transport. Vale and Kreis (1993) *Guidebook to the Cytoskeletal and Motor Proteins* New York: Oxford University Press; Alberts et al. (1994) *Molecular Biology of the Cell,* 788-858). Cytoskeletal proteins are found in all cells and are involved in the pathogenesis of a large range of clinical diseases. The cytoskeleton includes a collection of polymer proteins, microtubules, actin, intermediate filaments, and septins, as well as a wide variety of proteins that bind to these polymers (polymer-interacting proteins). Some of the polymer-interacting proteins are molecular motors (myosins, kinesins, dyneins) (Goldstein (1993) *Ann. Rev. Genetics* 27: 319-351; Mooseker and Cheney (1995) *Ann. Rev. Cell Biol.* 111: 633-675) that are essential for transporting material within cells (e.g., chromosomal movement during metaphase), for muscle contraction, and for cell migration. Other groups of proteins (e.g., vinculin, talin and alpha-actinin) link different filaments, connect the cytoskeleton to the plasma membrane, control the assembly and disassembly of the cytoskeletal polymers, and moderate the organization of the polymers within cells.

Given the central role of the cytoskeleton in cell division, cell migration, inflammation, and fungal/parasitic life cycles, it is a fertile system for drug discovery. Although much is known about the molecular and structural properties of cytoskeletal components, relatively little is known about how to efficiently manipulate cytoskeletal structure and function. Such manipulation requires the discovery and development of specific compounds that can predictably and safely alter cytoskeletal structure and function. However, at present, drug targets in the cytoskeleton have been relatively untapped. Previous studies have been directed towards drugs that interact with the cytoskeletal polymers themselves (e.g., taxol and vincristine), and towards motility assays. Turner et al. (1996) *Anal. Biochem.* 242 (1): 20-5; Gittes et al. (1996) *Biophys. J.* 70 (1): 418-29; Shirakawa et al. (1995) *J. Exp. Biol.* 198: 1809-15; Winkelmann et al. (1995) *Biophys. J.* 68: 2444-53; Winkelmann et al. (1995) *Biophys. J.* 68: 72S. In general, the studies on polymerization and motility were preliminary research studies performed in an effort to define the existing mechanisms of these actions. Although the cytoskeletal system has been characterized to some extent, studies have not focused on the binding interactions of the polymers such as microtubules and actin with various polymer binding proteins such as molecular motors with a specific goal of identifying and characterizing modulators of such interactions that could have biopharmaceutical and bioagricultural relevance. In particular, there is still a need in the art to identify compounds which can be used to manipulate the cytoskeletal system, particularly in regards to modifying the binding characteristics of the cytoskeletal components to one another. In particular, there is a need in the art to identify compounds that modulate the cytoskeletal binding interactions which can be used as therapeutics and/or diagnostics, as well as compounds which can be used in the bioagriculture field (e.g. as pesticides). It is noted that virtually no effort has been directed to finding agents (e.g. drugs) that target cytoskeletal proteins that bind to the different filaments and which are expected to provide targets of greater specificity and thereby provide fewer unwanted side effects when targeted with various modulators.

The invention herein provides convenient and rapid methods for identifying compounds not previously known to modulate cytoskeletal function. In particular, this invention provides assay methods that include methods for measuring binding interactions between cytoskeletal polymers and cytoskeletal polymer-binding proteins that can be applied to high-throughput screening to identify small molecules that modify this interaction. The methods described herein include methods that provide high sensitivity and can be used in complex mixtures, including, but not limited to crude cell extracts.

SUMMARY OF THE INVENTION

The present invention provides a method of identifying and characterizing compounds which modulate the binding of two cytoskeletal components. The methods are rapid, convenient and sensitive. Preferably, the method is used to identify lead compounds that can be used as therapeutics or diagnostics, or which can be used in the agricultural field.

In one embodiment, this invention provides high throughput assay (efficient screening of multiple samples) methods for testing multiple test agents (e.g., compositions and/or compounds) for their ability to modulate cytoskeletal function. The methods generally involve adhering a first cytoskeletal component to a solid support; contacting this first component with a second cytoskeletal component having an affinity for said first cytoskeletal component, in a (e.g. aqueous) reaction mixture; further contacting the reaction mixture with one or more, preferably multiple test compositions to determine their ability to modulate the binding affinity of the first and second cytoskeletal components; and detecting changes in the binding affinity of the second cytoskeletal component to the first cytoskeletal component at a test concentration and a control concentration (e.g., zero concentration) of said test compositions; wherein said detecting does not involve detecting the active movement of the cytoskeletal components. Detection can be by optical methods including, but not limited to total internal reflection microscopy or confocal microscopy.

The assays of the invention can be adapted to a wide variety of solid support, including, but not limited to glass, plastic surfaces, metal surfaces, or mineral (e.g., quartz or mica) surfaces. These assays are ideal for very high throughput screening for drugs that alter interactions between cytoskeletal polymers and their interacting proteins. Assays can be advantageously applied to a 96 well (or greater) plate format.

The invention particularly encompasses methods wherein the first cytoskeletal component is indirectly adhered to the solid support, if need be in an oriented fashion (see below); wherein the first cytoskeletal component is indirectly adhered to the solid support by binding to an inactivated molecular motor which is bound to the support, wherein the first cytoskeletal component forms multiple arrays on a single integrated support, wherein the second component is tagged with a reporter molecule, particularly a fluorophore such as GFP. Where fluorescence is detected, in a preferred embodiment the method of detection is total internal reflection microscopy. The assays can detect binding in the presence of a cytoskeletal polymer, of a monomer of a cytoskeletal polymer, or a molecular motor. In preferred embodiments, the signal to noise ratio is at least about 2-fold, more preferably at least about 4-fold. The density of the first cytoskeletal component on the solid support is at least 2 polymers/$50\mu^2$, the concentration of the first cytoskeletal component is at least 10 ng/$\mu^2$, and/or the throughput is at least about one sample/min.

In another embodiment this invention provides methods of identifying a lead compound (e.g., therapeutic or bioagricultural) that modulates activity of a cytoskeletal system. In this embodiment, the methods preferably involve providing an assay mixture comprising a first component of a microtubule system and a second component of a cytoskeletal system, wherein said first component and said second component have an affinity for each other; contacting the assay mixture with a test compound to be screened for the ability to modulate binding between the first component and the second component; detecting a difference in the binding specificity or avidity of the first component to the second component, at a test concentration and a control concentration of said compound to be screened, wherein said detecting does not involve detecting active movement of a component of said cytoskeletal system, and wherein the difference in the binding specificity or avidity or affinity of the first component to the second component identifies a compound that modulates activity of a cytoskeletal system.

In particularly preferred embodiments, the first and second components are selected from the group consisting of cytoskeletal polymers, motor proteins and cytoskeletal polymer binding proteins. Preferred first and second components can be components of an actin/myosin system, a tubulin system, or an intermediate filament system. Preferred first and second cytoskeletal components include binding pairs selected from Table 1. The reaction mixture can include a cell lysate. The methods can further involve entering the identity of a test compound that has a significant effect on binding of the first component to the second component into a database of therapeutic or bioagricultural lead compounds. Inclusion in the database can require that the test compound cause at least a 10% change in binding affinity or avidity between the first and second component. The assay can optionally additionally include contacting a cell with a test compound whose identity is entered in said database; and detecting inhibition in the growth or proliferation of the cell. In the assays described herein, the first component can be labeled with a label (e.g., a fluorescent label). Where the label produces an optical signal, detection is preferably by an optical method (e.g., microscopy).

The assay methods of this invention are well suited for high throughput screening. Thus, in preferred embodiments, at least 50 test compounds are screened simultaneously. Similarly, at least two different first component and second component pairs can be tested simultaneously. The test compounds can be members of a combinatorial library. In many assays, the first or second cytoskeletal components or said second components are attached to a solid support.

In still another embodiment, this invention provides methods of identifying a therapeutic lead compound that modulates activity of a cytoskeletal system, where the methods involve providing an assay mixture comprising a first component of a cytoskeletal system and a second component of a cytoskeletal system, wherein the first and said second components specifically bind to each other; contacting the assay mixture with a test compound to be screened for the ability to inhibit or enhance binding between the first and second component; and detecting a change in coupling between ATP hydrolysis and force generation; wherein said change indicates that said compound modulates activity of a cytoskeletal system. In a particularly preferred embodiment, the first and second components are not both tubulin or both actin or both tau protein, however, one of the two components can be tubulin, actin or tau protein;

In still another preferred embodiment, the method in accordance with the present invention comprises the step of providing at least one assay mixture comprising a first component of a cytoskeletal system and a second component of a cytoskeletal system, wherein the first component and the second component have an affinity for (e.g., specifically bind to) each other. This embodiment further comprises the step of contacting the assay mixture with at least one test compound to be screened for the ability to modulate binding between the first component and second component. Also included in this embodiment is the step of detecting a difference in the binding specificity or avidity of the first component to the second component, at a test concentration and a control concentration of the compound to be screened. A difference in the binding specificity or avidity indicates the presence of a compound that modulates activity of a cytoskeletal system.

In an embodiment in accordance with the present invention, the first and second components are selected from the group consisting of cytoskeletal polymers such as microtubules, actin and intermediate filaments, motor proteins such as kinesin, dynein and myosin and polymer binding proteins such as Op18, tau protein or microtubule associated proteins (MAPs). In one embodiment provided herein, wherein one of said cytoskeletal components is a cytoskeletal polymer, the other cytoskeletal component is not the same polymer. In another embodiment herein, wherein one cytoskeletal component is a tau protein, the other cytoskeletal component is not the same tau protein.

The assay mixture described in accordance with the invention can comprise a cell lysate. A single assay mixture or a plurality of assay mixtures can be provided. A single test compound can be provided to each assay mixture, or more than one test compound can be provided to each assay mixture. Wherein a plurality of assay mixtures are provided, one or more assay mixtures can comprise a test compound which differs from the test compound of another assay mixture.

In accordance with the invention provided herein, one of the components of the cytoskeletal system can be adhered directly or indirectly to a solid support. Alternatively, the components can be in solution.

In one embodiment, at least one of the first or second cytoskeletal components is labeled. The label can be selected from a wide variety of reporter molecules. Reporter molecules include fluorophores, fluorescent proteins, and epitope tags.

The detection binding affinity, avidity, or specificity can be accomplished by optical methods including, but not limited to plate readers and microscopy. Preferred microscopic methods include confocal or total internal reflection microscopy. In one embodiment, flow cytometry is used. Alternatively, the method of detection can be by a method of detecting enzymatic activity, e.g., an ATPase assay. Alternatively, the method of detection can be by determining protein interactions, i.e., a two hybrid system.

In a preferred embodiment, the difference in binding specificity, affinity or avidity detected is 10% or greater in either direction of that of the test concentration. In another embodiment, the difference from that of the test compound is or is greater than 20%, 40%, 60% or 80% in either direction. In an alternative embodiment, the difference from that of the test compound is or is greater than 100%, 200%, 300%, 500%, 800%, or 1000%. In one embodiment provided herein, the control concentration of the test compound is the absence of the test compound to be screened.

The compounds to be screened can be selected from any number of origins. The test compounds include, but are not limited to, proteins, peptides, peptidomimetics, peptoids, saccharides, nucleic acids (DNA and RNA), and small organic molecules. The compounds can be from a library of synthetic or natural product sources and may be from a library created using combinatorial techniques. Preferably, the test compound is a small molecule. The small molecule is preferably 4 kilodaltons (kd) or less. In another embodiment, the compound is less than 3 kd, 2 kd or 1 kd. In another embodiment the compound is less than 800 daltons (D), 500 D, 300 D or 200 D. In another embodiment wherein both of said components are in solution, a preferred method excludes single nucleotides as the compound to be screened. Alternatively, this embodiment excludes molecules which can be hydrolyzed by one of the cytoskeletal components to provide chemical energy. Another preferred embodiment excludes antibodies, particularly those previously known in the art to bind to cytoskeletal components. Another embodiment excludes inositol phosphates.

Definitions

"Test composition" (used interchangeably herein with "candidate agent" and "test compound" and "test agent") refers to an element molecule or composition whose effect on the interaction between two or more cytoskeletal components it is desired to assay. The "test composition" can be any molecule or mixture of molecules, optionally in a suitable carrier.

The terms "isolated" "purified" or "biologically pure" refer to material which is substantially or essentially free from components which normally accompany it as found in its native state.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "fusion protein" refers to a protein (polypeptide) composed of two polypeptides that, while generally unjoined in their native state, are joined by their respective amino and carboxyl termini through a peptide linkage to form a single continuous polypeptide. It will be appreciated that the two polypeptide components can be directly joined or joined through a peptide linker/spacer.

"Cytoskeletal function" refers to the biological roles of the cytoskeleton: to provide structural organization (e.g., microvilli, mitotic spindle) and to mediate motile events within the cell (e.g., muscle contraction, mitotic contractile ring; pseudopodal movement, active cell surface deformations, vesicle formation and translocation). Cytoskeletal activity infers involvement in cytoskeletal function. Cytoskeletal activity includes the binding interaction of two cytoskeletal components.

"Molecular motor" is a cytoskeletal molecule that utilizes chemical energy to produce mechanical force, and drives the motile properties of the cytoskeleton.

"Cytoskeletal component" denotes any molecule that is found in association with the cellular cytoskeleton, that plays a role in maintaining or regulating the structural integrity of the cytoskeleton, or that mediates or regulates motile events mediated by the cytoskeleton. This term includes cytoskeletal polymers and monomers thereof (e.g., actin filaments, microtubules, myosin filaments, 100 Å or intermediate filaments), molecular motors, and cytoskeleton associated regulatory proteins (e.g., tropomyosin, alpha-actinin).

"Cytoskeletal polymer" refers to homo and heteropolymers that form part of the cellular cytoskeleton (e.g., actin filaments, microtubules, myosin filaments, etc.)

"Cytoskeletal system" refers to a collection of cytoskeletal components including monomers of cytoskeletal polymers that are typically found associated with each other in vivo.

"A monomer of a cytoskeletal polymer" refers to the monomeric subunit of a cytoskeletal polymer, such as the alpha and beta tubulin subunits of microtubules, the G-actin subunit of actin filaments, the monomer of intermediate filaments, and the myosin subunits of myosin filaments.

An "actin/myosin system" refers to the collection cytoskeletal components, including monomers, typically associated with actin and/or myosin in vivo. Such components include, but are not limited to actin, myosin, actin binding proteins (e.g., ABP-50, ABP-120, ABP-280), actin depolymerizing factor (ADF), α-actinins, actobindin, actolinkin, annexins, caldesmons, calponin, capping proteins, cofilin, coronin, c-proteins, dematins, depactin, dystrophin, ezrin, fascin, fimbrin, gCap39, gelsolins, hisactophilin, insertin, MARCKS, myomesin and m-protein, nebulin, nuclear actin binding protein (NAB), paramyosin, ponticulin, profilins, proteins 4.1, radixin, sarcomeric m-creatine kinase, severin, small actin crosslinking proteins, spectrins, tenuin, thymosin β4 (Tβ4), titin, tropomodulin, tropomyosins, troponins, villin, vitamin D binding/Gc protein (DBP/Gc), 25 kDa inhibitor of actin polymerization (25 kDa IAP) and 43 kDa protein (see, e.g., Kreis and Vale (1995) *Guidebook to the cytoskeletal and motor proteins*. Oxford University Press, Oxford, U.K.).

A "tubulin system" refers to a collection of cytoskeletal components, including monomers, typically associated with tubulin in vivo. Such components include, but are not limited to tubulin, chartins, MAP1A, MAP1B/MAP5, MAP2, MAP3, MAP4 (MAP-U), MARPS, pericentrin, radial spoke proteins, microtubule motors, STOPs, syncolin, tau, α/β tubulin, γ-tubulin, tubulin tyrosine ligase (TTL), tubulin carboxypeptidase (TCP), X-MAP, 205K MAP, and the like (see, e.g., Keris and Vale (1995) *Guidebook to the cytoskeletal and motor proteins*. Oxford University Press, Oxford, U.K.).

An "intermediate filament system" refers to a collection of cytoskeletal components, including monomers, typically associated with intermediate filaments in vivo. Such components include, but are not limited to intermediate filaments, cytokeratins, desmin, epinemin, filaggrins, filensin, GFAP, α-internexin, lamins, nestin, neurofilament triplet proteins (e.g. NF-L, NF-M, NF-H), paranemin, peripherin, plectin, synemin, vimentin, and the like (see, e.g., Keris and Vale (1995) *Guidebook to the cytoskeletal and motor proteins*. Oxford University Press, Oxford, U.K.).

"Solid support" means any solid surface, such as a bead or planar glass, a flexible or stiff membrane, a plastic, metal, or mineral (e.g., quartz or mica) surface, to which a molecule may be adhered. The solid support can be planar or have simple or complex shape. The surface to which the molecule is adhered can be an external surface or an internal surface of the solid support. Particularly where the surface is porous, the molecule is likely to be attached to an internal surface.

"Adhered to" or "attached" to a solid support denotes that one of said first or second cytoskeletal components is directly or indirectly fixed to the solid substrate and that more than 95% of the first cytoskeletal component remains associated with the solid support at least until all the manipulations are completed and the level of binding is assessed.

"Adhered or attached in an oriented fashion" means that essentially all the individual cytoskeletal components that bind to the solid support do so at some defined site or domain of the cytoskeletal component, such that a second site of the molecule (e.g., a catalytic domain) can freely interact with molecules.

"Spatially arranged to form distinct arrays" means that the cytoskeletal component or components that adhere to the solid support are laid out in precise patterns, such as rows of dots, or rows of squares, or lines.

"Modulate" means to increase or decrease (e.g. binding affinity, and/or avidity and/or specificity) relative to a control or test concentration. In one embodiment, the difference in binding specificity, or affinity, or avidity detected is at least 10%, or alternatively at least 20%, or alternatively at least 40%, or alternatively at least 60% or alternatively at least 80% in either direction (increased or decreased). In an alternative embodiment, the difference in affinity or avidity of the control from that of the test compound is or is greater than 100%, 200%, 300%, 500%, 800%, or 1000%.

"Binding specificity" refers to the extent that a first molecule binds to a second molecule in relation to whether the first molecule will also bind to other (third, fourth and so on) molecules. The binding specificity can be determined by an in vitro binding assay according to standard techniques known in the art. In a preferred embodiment, the phrase "binding specificity" or "specifically binds to" or when referring to a cytoskeletal component refers to a binding reaction which is determinative of the presence of the protein or in the presence of a heterogeneous population of proteins and other biologics. Thus, under designated assay conditions, a specified molecule (e.g. an antibody specific for a cytoskeletal component) binds to a particular cytoskeletal component and does not bind in a significant amount to other proteins present in the sample.

The phrase "having an affinity for" in the context of a first cytoskeletal component having an affinity for a second cytoskeletal component refers to the tendency of the first and second cytoskeletal components to associate with each other in vivo. The association can be permanent or transient and is typically characterized by a change in one or more physical and/or chemical properties of one or both of the components. In some preferred embodiments, the components that have an affinity for each other specifically bind to each other.

"Binding avidity" as used herein is the strength of interactions between multivalent components. Determinations of binding avidity are known in the art as described at page 124 in Kuby (1992) *Immunology*, W.H. Freeman and Company, New York.

"Binding affinity" as used herein refers to the strength of the sum of total of noncovalent interactions between two molecules. Determinations of binding affinity are known in the art as described at pages 122-124 in Kuby (1992) *Immunology*, W.H. Freeman and Company, New York.

"Active movement" is movement that requires and utilizes chemical energy (as opposed to Brownian motion, passive dispersion, etc.).

"Reporter molecule" denotes a molecule that can be detected either visually (e.g., because it has color, or generates a colored product, or emits fluorescence) or by use of a detector that detects properties of the reporter molecule (e.g., radioactivity, magnetic field, etc.). In one embodiment, reporter molecules allow for the detection of the interaction of two molecules. Reporter molecules include labels (including ligands) which allows for detection, such as a radiolabel, fluorophores, chemiluminescence, biotin, streptavidin, digoxigenin, anti-digoxigenin, sugars, lectins, antigens, and enzyme conjugates. The reporter molecule can be a protein that can be used as a direct or indirect label, i.e., green fluorescent protein (GFP), blue fluorescent protein (BFP), yellow fluorescent protein (YFP), red fluorescent protein (RFP), luciferase, β-galactosidase, all commercially available, i.e., Clontech, Inc. Moreover, one embodiment utilizes molecules that change their fluorescence or activity upon a change in binding.

In one embodiment, "detecting the binding" means assessing the amount of a given second component that binds to a given first component in the presence and absence of a test composition. This process generally involves the ability to assess the amount of the second component associated with a known fixed amount of the first component at selected intervals after contacting the first and second components. This may be accomplished by attaching to the second component a molecule or functional group that can be visualized or measured (e.g., a fluorescent moiety, a radioactive atom, a biotin that can be detected using labelled avidin) or by using ligands that specifically bind to the second component. The level of binding is detected quantitatively.

"A compound that binds to both the solid support and to the first cytoskeletal component" refers to a compound that binds to the substrate essentially irreversibly, preferably through a covalent bond or through a multivalent attachment, and to the first cytoskeletal component with high affinity (an effective $K_D$=at least $10^{-8}$, preferably at least $10^{-10}$, most preferably at least $10^{-12}$). "Effective $K_D$" refers to situations wherein there are multiple attachment sites between two cytoskeletal components; the binding of multiple sites, each of which has lower affinity, provides for binding with an overall effective affinity makes it seem like the binding affinity of the interaction between the two components is higher than it is.

A "therapeutic" as used herein refers to a compound which is believed to be capable of modulating the cytoskeletal system in vivo which can have application in both human and animal disease. Modulation of the cytoskeletal system would be desirable in a number of conditions including but not limited to: abnormal stimulation of endothelial cells (e.g., atherosclerosis), solid and hematopoetic tumors and tumor metastasis, benign tumors, for example, hemangiomas, acoustic neuromas, neurofibromas, pyogenic granulomas, vascular malfunctions, abnormal wound healing, inflammatory and immune disorders such as Rheumatoid Arthritis, Bechet's disease, gout or gouty arthritis, abnormal angiogenesis accompanying: rheumatoid arthritis, psoriasis, diabetic retinopathy, and other ocular angiogenic diseases such as, macular degeneration, corneal graft rejection, corneal overgrowth, glaucoma, Osler Webber syndrome, cardiovascular diseases such as hypertension, cardiac ischemia and systolic and diastolic dysfunction and fungal diseases such as aspergillosis, candidiasis and topical fungal diseases such as tinea pedis.

A "diagnostic" as used herein is a compound that assists in the identification and characterization of a health or disease state. The diagnostic can be used in standard assays as is known in the art.

A "bioagricultural compound" as used herein refers to a chemical or biological compound that has utility in agriculture and functions to foster food or fiber crop protection or yield improvement. For example, one such compound may serve as a herbicide to selectively control weeds, as a fungicide to control the spreading of plant diseases, as an insecticide to ward off and destroy insect and mite pests. In addition, one such compound may demonstrate utility in seed treatment to improve the growth environment of a germinating seed, seedling or young plant as a plant regulator or activator.

The phrase "coupling between ATP hydrolysis and force generation" refers to the fact that many molecular motors are effective ATPases hydrolyzing ATP to ADP to provide energy for force generation. The ATPase activity of the motor is often increased dramatically when the motor binds to another cytoskeletal component such as a microtubule. An alteration in the relationship between motor binding or force generation and ATP hydrolysis is a change in "coupling between ATP hydrolysis and force generation."

It is understood that the definitions which apply to the cytoskeletal system apply to embodiments which are drawn to specific components of the cytoskeletal system.

DETAILED DESCRIPTION

Figure 1:
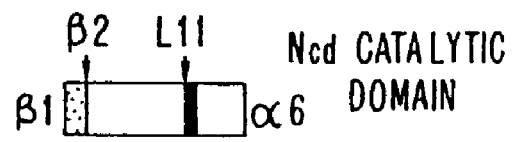
FIG. 1 shows diagrams of different kinesin-GFP chimeras.
Figure 1:
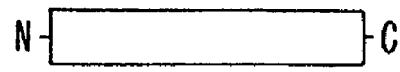
Figure 1:
Figure 1:
Figure 1:
Figure 1:
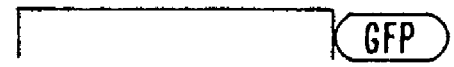
Figure 1:
Figure 1:
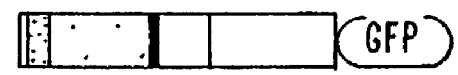
Figure 2:
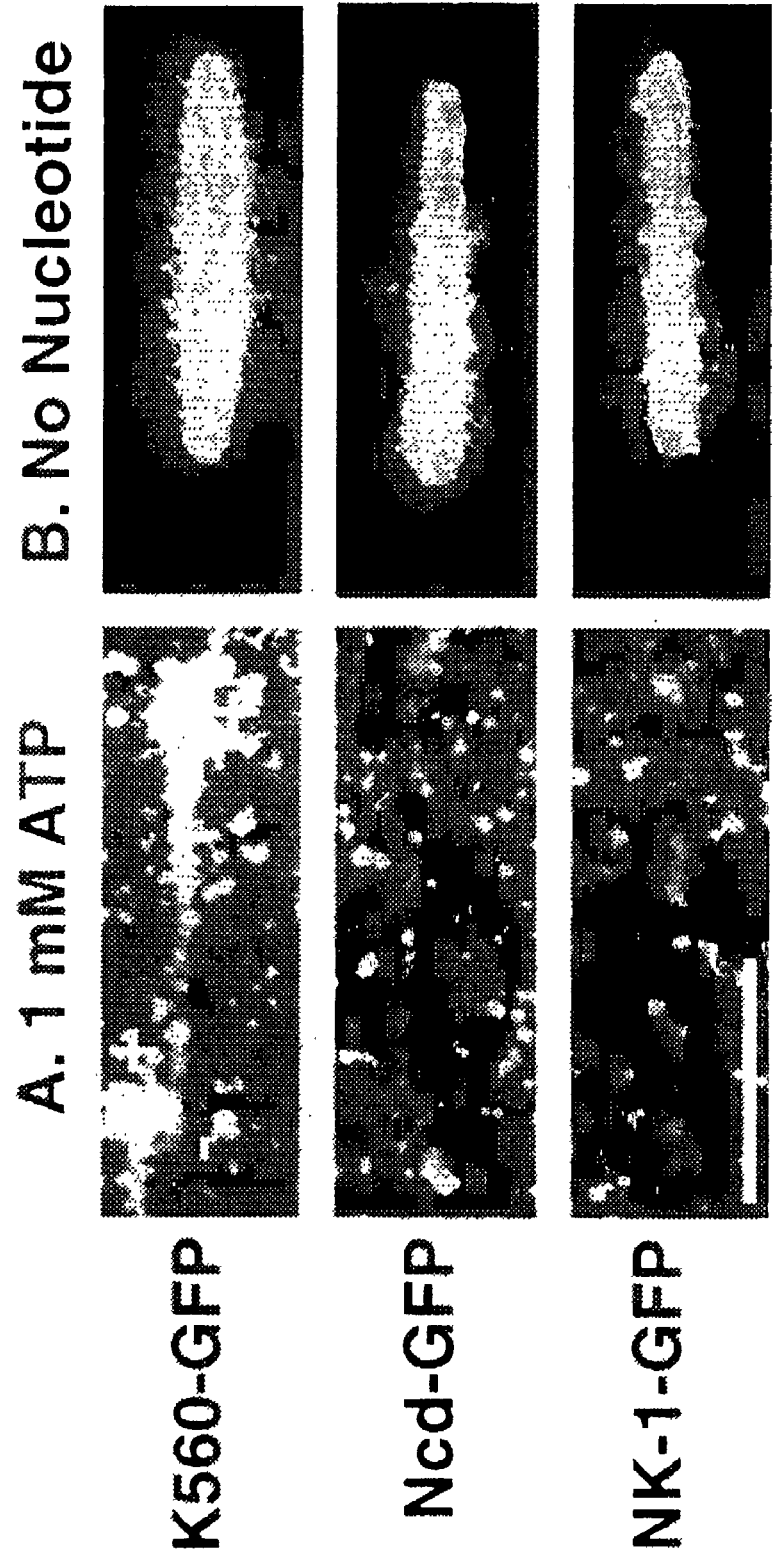
FIG. 2 illustrates binding interactions between fluorescent motors (green fluorescent protein fused to kinesin (K560-GFP), Ncd (Ncd-GFP), or a motor chimera (NK-1-GFP)) and microtubule polymers. Binding interactions are shown in ATP (a low affinity state) and no nucleotide (a high affinity state). Imaging was performed using total internal reflection microscopy. Differences in fluorescent motor binding to the surface-bound microtubule can be detected and quantitated by fluorescence intensity.

Provided herein are assays for the purpose of identifying compounds that modulate the cytoskeletal system. In preferred embodiments, the assays effectively screen and identify agents that increase or decrease interactions that normally occur between components of the cytoskeletal system (e.g. actin/myosin interactions, etc.). It was a discovery of this invention that cytoskeletal component interactions, in one particularly preferred embodiment, motor/track and accessory protein interactions provide novel targets for screening for compounds that are useful as animal therapeutics, bioagricultural agents, and the like. Unlike assays for agents that target highly conserved molecules (e.g., tubulin), in preferred embodiments. the assays of this invention identify agents that specifically target relatively variable molecules (e.g., motors and/or accessory proteins) and thus provide a means for modulating cytoskeletal activity with a specificity (e.g., species an/or tissue specificity) hitherto unknown. As is described in further detail below, the assays provide for the convenient use of a number of different cytoskeletal components and assay formats. Moreover, any compound can be tested rapidly and efficiently.

I. Assays for Modulators of Cytoskeletal Component Interactions.

The assay methods of this invention generally involve either identifying binding interactions between one or more test agents and a component of a cytoskeletal system, or, more preferably identifying the effect of one or more test agents on the binding interactions between two (or more) components of a cytoskeletal system. The assays can be performed in solution or in solid phase, as individual assays or in highly parallel (e.g. high throughput) modalities, and with single or multiple test agents.

A variety of different assays for detecting compounds and compositions capable of binding to a cytoskeletal component and of modulating the binding of a second cytoskeletal component to a first cytoskeletal component are used in the present invention. For a general description of different formats for binding assays, including competitive binding assays and direct binding assays, see *Basic and Clinical Immunology*, 7th Edition (D. Stites and A. Terr, ed.) (1991); *Enzyme Immunoassay*, E. T. Maggio, ed., CRC Press, Boca Raton, Fla. (1980); and "Practice and Theory of Enzyme Immunoassays," in P. Tijssen, *Laboratory Techniques in Biochemistry and Molecular Biology*, Elsevier Science Publishers, B.V. Amsterdam (1985).

A) Direct Binding Assays.

In direct binding assays the ability of one or more test compositions to bind to a cytoskeletal component (e.g. actin, myosin, kinesin, tubulin, etc.) including, but not limited to the components identified in Table 1, is assayed. Simple binding assays are well known to those of skill in the art. In one embodiment, either the test composition (agent) or the cytoskeletal component is labeled, the component and the agent are contacted with each other and the association of the labeled moiety (component or agent) with the other binding partner (cytoskeletal component where the test agent is labeled and test agent where the cytoskeletal component is labeled) is detected and/or quantified. Alternatively, both the cytoskeletal component and the test agent can both be labeled and the association of the labels then indicates binding. The use of fluorescent labels capable of fluorescence resonance energy transfer (FRET) greatly facilitates the detection of such an association (e.g., the fluorescence of the labels is typically quenched when they are brought into proximity to each other, see, e.g., Stryer (1978) *Ann. Rev. Biochem.*, 47: 819-846.).

Direct binding assays can also be performed in solid phase where either the test agent(s) or the cytoskeletal component is immobilized on a solid support. When the cytoskeletal component is immobilized it is contacted with the test agent(s) (optionally labeled) and conversely where test agent(s) are immobilized they are contacted with the cytoskeletal component(s) (optionally labeled). After washing away unbound test agent and/or cytoskeletal component, remaining bound test agent/cytoskeletal component complexes indicate binding of the test agent(s) to the cytoskeletal component. Where the non-immobilized test agent or cytoskeletal component was labeled, detection of the label associated with the solid support provides a measure of test agent/cytoskeletal component binding. Fluorescence resonance energy transfer systems (FRET) are suitable for use in the solid phase as well.

Neither test agent nor cytoskeletal component need be labeled prior to the assay. An "indirect" subsequently applied label (e.g. a labeled antibody specific for the cytoskeletal component or test agent(s)) can be used to detect the test agent/cytoskeletal component in the test agent/cytoskeletal component complex.

It will be appreciated that neither test agent nor cytoskeletal component need be labeled in the assays. Other means of detecting complex formation are known to those of skill in the art (e.g. electrophoresis, density gradient centrifugation, etc.).

B) Two-Component Inhibition Assays.

In "two-component inhibition assays", the test agent(s) are assayed for their ability to alter the binding affinity, specificity or avidity between two (or more) components of a cytoskeletal system. In general terms, one or both of the two components of a cytoskeletal system (or of two different cytoskeletal systems) are contacted with a test agent. The binding affinity or avidity of the two components is compared to the same assay performed at a different (control) concentration of test agent. A difference in the binding affinity, specificity, or avidity of the two cytoskeletal components indicates that the test agent effects cytoskeletal function.

The "test" agent can be contacted with one or both of the components of a cytoskeletal system before the two components contact each other, at the same time, or after the two components have been allowed to contact each other.

A wide variety of assays suitable for detecting the effect of test agent(s) on binding of two components of biological systems are well known to those of skill in the art. In preferred embodiments, such assays are "competitive" in format where the test agent is screened for the ability to compete with a second cytoskeletal component for specific binding sites on a first cytoskeletal component and thereby alter the binding between the two cytoskeletal components. However, it is recognized that the test agent need not bind either of the cytoskeletal components in order to effect changes (in the conformation or the chemical constitution of one or both of the cytoskeletal components and thereby alter their binding interaction. Regardless of the specific mechanism of action of the test agent, the assays described below are generally designed to reveal alterations in the binding specificity, affinity, or avidity of the cytoskeletal components.

In one preferred embodiment, the test agent(s) are assayed relative to a control assay. The control assay can contain the test agent(s) at a different concentration or one or more particular test agent(s) can be absent from the control assay. A difference (preferably a statistically significant difference) in the cytoskeletal component binding between the test and the control assays indicates that the test agent has an effect on cytoskeletal function. An increase or decrease in binding by at least 10%, more preferably by at least 20%, most preferably by at lease 50%, 80%, 90% or more is preferred to record a positive result (indicating test agent activity) in an assay.

In yet another embodiment, one of the cytoskeletal components has a detectable moiety attached thereto, i.e., fluorescence, which changes in intensity, spectrum or polarization upon different binding thereto, i.e., the fluorescence changes upon a second agent binding thereto. In yet another embodiment, a conjugate such as a phosphatase is used such that binding is measured upon adding substrate on which the enzyme can act. Moreover, it is understood that magnetic beads and the like can be used.

In an alternative embodiment, the binding affinity between a first cytoskeletal component and a second cytoskeletal component is determined in the presence and absence of a test agent. A difference in the binding affinity indicates the identification of a compound which modulates the cytoskeletal system. The invention also provides for the identification of a compound which modulates the binding of a cytoskeletal component to another cytoskeletal component.

1) "Competitive" Assays.

In "competitive" assays the test agent is assayed by contacting the agent with either or both of two components of a cytoskeletal system (a first component e.g. a motor, and a second component, e.g. a "track") that typically associate together. The effect of the test agent on the cytoskeletal system is then assayed by assessing the amount of second cytoskeletal component associated with the first cytoskeletal component. Where the test agent actually competes with the for binding to one or more of the cytoskeletal components or otherwise inhibits binding, the amount of a second cytoskeletal component associated with the first cytoskeletal component is diminished relative to a control assay having a lower concentration of the particular test agent or lacking that test agent at all.

Conversely, "agonistic" test agents may increase the binding affinity, avidity, or specificity of the two cytoskeletal components. In this instance, an increase the amount of a second cytoskeletal component associated with the first cytoskeletal component is increased relative to a control assay having a lower concentration of the particular test agent or lacking that test agent at all.

The amount of inhibition or stimulation of binding of a cytoskeletal component by the test compound depends on the binding assay conditions and on the concentrations of cytoskeletal components, and test agent(s) used. Under specified assay conditions, a test agent is said to be capable of inhibiting or enhancing the binding of a second cytoskeletal component to a first cytoskeletal component if the amount of bound second cytoskeletal component is decreased or increased, respectively, by a statistically significant amount. An increase or decrease in binding by at least 10%, more preferably by at least 20%, most preferably by at lease 50%, 80%, 90% or more is preferred to record a positive result (indicating test agent activity) in an assay.

As indicated above, those skilled in the art understand that to affect the binding between two cytoskeletal components, the test component need not compete with the cytoskeletal components for a specific binding site. Therefore, in an embodiment herein, the modulator may induce a change in the conformation of the binding site so as to increase or decrease binding.

As indicated above, the assays can be performed in solution or in solid phase. In a preferred solid phase assay, one of the cytoskeletal components is attached to a solid support. The second cytoskeletal component is then contacted with the first cytoskeletal component either prior to or after one or both components are exposed (contacted with) the test agent(s). After an appropriate wash step, the amount of cytoskeletal component bound is assayed, e.g., as described below.

The amount of binding of the second cytoskeletal component to the first cytoskeletal component can be assessed by directly labeling the second component with a detectable moiety, or by detecting the binding of a labeled ligand that specifically binds to the second cytoskeletal component. A wide variety of labels may be used. The component may be labeled by any one of several methods. Traditionally, a radioactive label ($^3$H, $^{125}$I, $^{35}$S, $^{14}$C, $^{32}$P) is used. Non-radioactive labels include fluorophores, chemiluminescent agents, enzymes, and antibodies. The choice of label depends on sensitivity required, ease of conjugation with the compound, stability requirements, and available instrumentation. A preferred fluorophore is a fluorescent protein (e.g. GFP). For a review of various labeling or signal producing systems which may be used, see U.S. Pat. No. 4,391,904.

2) FRET Assays.

As indicated above, fluorescent resonance energy transfer (FRET) systems can also be used to assay protein protein interactions. In FRET-based assays, both components (e.g. both cytoskeletal components) are labeled with fluorescent labels. The absorption and emission spectra of the labels are selected such that one label emits at a wavelength that the other absorbs. When the labels are brought into proximity to each other (e.g., by binding of the two cytoskeletal components to each other) they quench thereby decreasing the fluorescence of the mixture. FRET is a powerful technique for measuring protein-protein associations and has been used previously to measure the polymerization of monomeric actin into a polymer (Taylor et al. (1981) *J. Cell Biol.*, 89: 362-367) and actin filament disassembly by severing (Yamamoto et al. (1982) *J. Cell Biol.*, 95: 711-719), but has not been used to screen for agents that modulate cytoskeletal component interactions.

Other assays can detect changes in fluorescence polarization.

3) Liquid Crystal Assay Systems.

In still another embodiment, binding of the two components of the cytoskeletal system can be detected by the use of liquid crystals. Liquid crystals have been used to amplify and transduce receptor-mediated binding of proteins at surfaces into optical outputs. Spontaneously organized surfaces can be designed so that a first cytoskeletal component, upon binding to a second cytoskeletal component (e.g. microtubules) hosted on these surfaces, trigger changes in the orientations of 1- to 20-micrometer-thick films of supported liquid crystals, thus corresponding to a reorientation of ~$10^5$ to $10^6$ mesogens per protein. Binding-induced changes in the intensity of light transmitted through the liquid crystal are easily seen with the naked eye and can be further amplified by using surfaces designed so that protein-ligand recognition causes twisted nematic liquid crystals to untwist (see, e.g., Gupta et al. (1998) *Science*, 279: 2077-2080). This approach to the detection of ligand-receptor binding does not require labeling of the analyte, does not require the use of electroanalytical apparatus, provides a spatial resolution of micrometers, and is sufficiently simple that it is useful in biochemical assays and imaging of spatially resolved chemical libraries.

4) ATPase Assay

In an alternative embodiment, used to identify agents that modulate binding of cytoskeletal components, an ATPase assay can be used. For example, molecular motors are effective ATPases hydrolyzing ATP to ADP to provide energy for force generation. The ATPase activity of the motor is often increased dramatically when the motor binds to another cytoskeletal component such as a microtubule. By examining ATP hydrolysis from a molecular motor in the presence of varying concentrations of test compounds which may effect binding between two cytoskeletal components, the binding can be quantified, thereby identifying novel agents which modulate binding. This assay has not been done to identify binding modulators.

One such ATPase assay is described in the examples below. In one preferred embodiment, the ATPase activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 µL of reaction is quenched in 90 µl of cold 0.3 M PCA. Phosphate standards are used so data can be converted to mM inorganic phosphate released.

When all reactions and standards have been quenched in PCA, 100 µl of malachite green reagent is added to the to relevant wells in e.g., a microtiter plate. The mixture is developed for 10-15 minutes and the plate is read at an absorbance of 650 nm. If phosphate standards were used, absorbance readings can be converted to mM Pi and plotted over time.

5) Protein Protein Interaction (e.g. Two-Hybrid) Assay.

In yet another embodiment, protein-protein interactions are used. For example, a two-hybrid system as known in the art can be used. The two-hybrid system is a method used to identify and clone genes for proteins that interact with a protein of interest. Briefly, the system indicates protein-protein interaction by the reconstitution of GAL4 function, which is detectable and only occurs when the proteins interact. This system and general methodologies concerning the transformation of yeast with expressible vectors are described in Cheng-Ting et al. (1991) *Proc. Natl. Acad. Sci. USA*, 88:9578-9582, Fields and Song (1989) *Nature*, 340: 245-246, and Chevray and Nathans, (1992) *Proc. Natl. Acad. Sci. USA*, 89: 5789-5793.

C) Assaying Multiple Agents.

While each assay mixture can be utilized to assay the effect of a single test agent, it will be recognizes that multiple test agents can also be screened in a single assay mixture. In such a multi-agent assay embodiment, two or more, preferably 4 or more, more preferably 16 or more and most preferably 32, 64, 128, 256, or even 512 or more agents are screened in a single assay reaction mixture. A positive result in that assay indicates that one or more of the combined agents are modulators of cytoskeletal function. In this instance, in a preferred embodiment, the method is repeated wherein the candidate agents are separated out to identify the modulator individually, or to verify that the agents work in conjunction to provide the difference in binding specificity, affinity, or avidity. Thus, for example, an assay originally run with 16 test agents may be re-run as four assays each containing four of the original 16 test agents. Again those assays testing positive can be divided and re-run until the agent or agent(s) responsible of the positive assay result are identified.

It is also noted that multiple test agents can be assayed together to identify agents that are additive or even synergistic in their effect on a cytoskeletal system, or conversely, to identify test agent(s) that are antagonistic in their effects on a cytoskeletal system.

In one embodiment, the method further comprises the step of entering the identity of a test compound which has been identified to modulate activity of a cytoskeletal system in accordance with the present invention into a database of therapeutic, diagnostic or bioagricultural lead compounds. In some cases it may be desirable to perform further assays on the compounds which have been identified herein. For example, activity of the identified compounds can be further assessed in areas other than their ability to modulate binding. For example, their ability to affect growth or proliferation of cells, particularly tumor cells, vesicle migration, mitosis, congression, filament movement, motility, etc. can be assessed.

D) High Throughput Screening.

In one embodiment, the assays of the present invention offer the advantage that many samples can be processed in a short period of time. For example, plates having 96 or as many wells as are commercially available can be used. In addition, the cytoskeletal components can be attached to solid supports and spatially arranged to form distinct arrays, such as rows of dots or squares, or lines. This, coupled to sophisticated masking, assay and readout machines greatly increase the efficiency of performing each assay and detecting and quantifying the results. It is possible with current technologies to efficiently make vast numbers ($10^6$ or more) of peptides having specified sequences and array them at distinct locations in a chip, and then to detect fluorescent associated with each position of the chip. See, e.g., U.S. Pat. No. 5,143,854; PCT Publication Nos. WO 90/15070, WO 92/10092 and WO 93/09668; and Fodor et al. (1991) *Science*, 251, 767-77.

Conventionally, new chemical entities with useful properties (e.g., inhibition of myosin tail interactions) are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of compounds (test compounds) potentially having the desired activity. Such "combinatorial chemical libraries" are then screened in one or more assays, as described herein, to identify those library members (particular chemical species or subclasses) that display a desired characteristic activity (e.g., therapeutic or bioagricultural). The compounds thus identified can serve as conventional "lead compounds" or can themselves be used as potential or actual therapeutics or bioagricultural agents.

Any of the assays for the test compounds and compositions described herein are amenable to high throughput screening. These assays detect inhibition of the characteristic activity of the cytoskeletal component, or inhibition of or binding to a receptor or other transduction molecule that interacts with the cytoskeletal component.

High throughput assays for the presence, absence, or quantification of particular nucleic acids or protein products are well known to those of skill in the art. Binding assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc., Fullerton, Calif.; Precision Systems, Inc., Natick, Mass., etc.) These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for the various high throughput assays. Thus, for example, Zymark Corp. provides technical bulletins describing screening systems for detecting the modulation of gene transcription, ligand binding, and the like.

In a preferred embodiment of this invention, the signal to noise ratio is relatively high (the signal is at least about 4-fold, preferably about 10-fold, and more preferably about 100 fold above background). Where the first cytoskeletal component on the solid support is a polymer (e.g., F-actin or microtubule), the density of is at least 2, preferably at least 10, more preferably at least 100, most preferably at least 1000 polymers/$50\mu^2$, wherein the average length of the polymers is $1\mu$. The concentration of the cytoskeletal component is at least 10, preferably at least 100, and more preferably at least 1000 ng/$\mu^2$. The desired high throughput rate averages at least about one, preferably at least about 10, and more preferably at least about 100 different test agents/min.

II. Assay Components.

A) Cytoskeletal Components

The number and identity of cytoskeleton components that have been identified thus far are legion, and far too numerous to be completely listed here. A partial listing can be found in the following references: Vale and Kreis (1993) *Guidebook to the Cytoskeletal and Motor Proteins* New York: Oxford University Press; Goldstein (1993), *Ann. Rev. Genetics* 27: 319-351; Mooseker and Cheney (1995) *Annu. Rev. Cell Biol.* 11: 633-675; Burridge et al. (1996), *Ann. Rev. Cell Dev. Biol.* 12: 463-519. Of special interest are components associated with the actin filament system (e.g., actin, myosin, tropomyosin, α-actinin, thymosin, profilin, spectrin, ankyrin, fimbrin, filamin, vinculin, villin, gelsolin, severin), with the microtubule system (alpha and beta tubulin, dynein, kinesin, MAPS, tau), and with the intermediate filaments (keratins, vimentin, neurofilament proteins, lamins, desmin). Although the assays of the invention will often focus on interactions between cytoskeletal components from the same filament subsystem (e.g., actin and actin-binding proteins), it should be noted that the different filament systems are integrated and that some components bridge more than one system and therefor components from two different systems can utilized in an assay of this invention.

In a preferred embodiment herein, the first and second components are selected from the pairs shown in Table 1.

TABLE 1

Pairwise combinations of cytoskeletal interactions.

| | |
|---|---|
| Actin Depolymerizing Factor/Cofilin | Actin |
| Adducin | Actin |
| Alpha actinins | Actin |
| Alpha catenin | Actin |
| Annexins | Actin |
| Adenomatous Polyposis Coli Protein | Tubulin/Microtubules |
| Arp 2/3 | Actin |
| Axonemal Dynein | Tubulin/Microtubules |
| Bipolar Kinesin | Tubulin/Microtubules |
| BPAG1 | Intermediate Filaments |
| Caldesmon | Actin |
| Capping Protein | Actin |
| Cardiac Muscle Myosin | Actin |
| CENP-E | Bub1 |
| CENP-E | CENP-F |
| Centrosomin | Tubulin/Microtubules |
| Chromokinesin | Tubulin/Microtubules |
| CLIP-170 | Tubulin/Microtubules |
| Coronin | Actin |
| Cortexillins | Actin |
| C-terminal Motor Domain Kinesin | Tubulin/Microtubules |
| Cytoplasmic Dynein | Tubulin/Microtubules |
| Cytoplasmic Myosin II | Actin |
| Dynactin Complex | Dynein |
| Dystrophin/Utrophin | Actin |
| ERM proteins: Ezrin, Radixin and Moesin | Actin |
| Filaggrins | Intermediate Filaments |
| Gamma Tubulin | Tubulin/Microtubules |
| Gelsolins | Actin |
| Heterotrimeric Kinesin | Tubulin/Microtubules |
| IFAP 300 | Intermediate Filaments |
| Internal Motor Domain Kinesin | Tubulin/Microtubules |
| Katanin | Tubulin/Microtubules |
| MAP1A | Tubulin/Microtubules |
| MAP1B-MAP5 | Tubulin/Microtubules |
| MAP2 | Tubulin/Microtubules |
| MAP4 | Tubulin/Microtubules |
| MARCKS | Actin |
| MARK Protein Kinases | Tubulin/Microtubules |
| Mitotic Kinesin | Tubulin/Microtubules |
| Monomeric Kinesin | Tubulin/Microtubules |
| Myosin Heavy Chain Kinases | Myosin |
| Myosin I | Actin |
| Myosin IX | Actin |
| Myosin Light Chain Kinases | Myosin Light Chains |
| Myosin V | Actin |
| Myosin VII | Actin |
| NuMa | Tubulin/Microtubules |
| Op18/Stathmin | Tubulin/Microtubules |
| Pericentrin | Tubulin/Microtubules |
| Plectin | Intermediate Filaments |
| Profilin | Actin |
| Protein 4.1 | Actin |
| Severin | Actin |
| Smooth Muscle Myosin | Actin |
| Spectrins | Actin |
| STOPS | Tubulin/Microtubules |
| Syncolin | Tubulin/Microtubules |
| Talin | Actin |
| Tau Protein | Tubulin/Microtubules |
| Tensin | Actin |
| Thymosin beta 4 | Actin |
| Tropomodulin | Actin |
| Tropomyosin | Actin |
| Troponins | Actin |
| VASP | Actin |
| Villin | Actin |
| Vimentin | Intermediate Filaments |
| Vinculin | Actin |
| WASP | Actin |
| XMAP215/TOG | Tubulin/Microtubules |
| ZW10 | Dynamitin |
| ZW10 | Rough Deal |
| Actophorin | Actin |
| Zyxin | Actin |
| Merlin | Actin |

TABLE 1-continued

Pairwise combinations of cytoskeletal interactions.

| | |
|---|---|
| Desmoplakin | Vimentin |
| Zonula Occludin-1 | Actin/spectrin |
| Depactin | Actin |
| Ankyrin | Intermediate Filaments/spectrin |
| DNase | Actin |
| Filamin/Plastin | Actin |
| Fimbrin | Actin |
| ActA | Actin |
| KIF | Tubulin/Microtubules |
| ABP-120 | Actin |
| EB1 | Tubulin/Microtubules |
| KIFs | Tubulin/Microtubules |
| Cdc42 | Actin |

In an alternative embodiment provided herein, the first component differs from the second component. By "differs", this includes embodiments wherein the components are the same but for a chemical modification of one but not the other. Moreover, if two components belong to the same class of cytoskeletal components, i.e., are both kinesins, but are distinct from one another based on their amino acid sequence, they are considered to differ from one another.

The cytoskeletal components of this invention can be recombinantly expressed using standard methods well known to those of skill in the art. Alternatively, the cytoskeletal components can obtained by purification from natural sources as explained below.

In general, the cytoskeletal components of this invention may be purified to substantial purity from natural and recombinant sources by known protocols using standard techniques (Vale and Kreis (1993), *Guidebook to the Cytoskeletal and Motor Proteins* New York: Oxford University Press), including differential extraction, selective precipitation with such substances as ammonium sulfate, column chromatography, immunopurification methods, and others. See, for instance, Scopes (1982) *Protein Purification: Principles and Practice*, Springer-Verlag: New York. For example, cytoskeletal proteins and polypeptides produced by recombinant DNA technology may be purified by a combination of cell lysis (e.g., sonication) and affinity chromatography or immunoprecipitation with a specific antibody to cytoskeletal components. For fusion products, subsequent digestion of the fusion protein with an appropriate proteolytic enzyme releases the desired polypeptide. The proteins may then be further purified by standard protein chemistry techniques.

The assays of the present invention also support the use of unpurified cytoskeletal components (e.g., cell lysates). Wherein a cell lysate is present, the lysate can be from any cell type (e.g., prokaryotic, eukaryotic, vertebrate, invertebrate and mammalian, etc.) Where unpurified preparations are used, detection of cytoskeletal component interaction preferably involves the use of detection systems specific for at least one of the cytoskeletal components studied.

B) Labeling of Cytoskeletal Components and/or Test Agent(s).

In one embodiment, the cytoskeletal component and/or the test agent(s) are labeled. Detectable labels suitable for use in the assays of this invention include any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others such as those commonly used in an ELISA), and colorimetric labels such as colloidal gold or colored glass or plastic (e.g. polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc., and fluorescent proteins (e.g., GFP). Chemiluminescent compounds include, but are note limited to, luciferin, and 2,3-dihydrophthalazinediones, e.g., luminol. For a review of various labeling or signal producing systems that may be used, see, U.S. Pat. No. 4,391,904.

C) Solid Supports

As indicated above in one embodiment, the assays of this invention are performed in the solid phase (e.g. with a test agent or a cytoskeletal component attached to a solid support). The "solid support" can be made of any material to which a molecule may be adhered that is compatible with the conditions and solutions for performing the binding assays. Examples include beaded or planar glass, metals, plastics, or minerals (e.g., mica or quartz). The supports can be relatively rigid, formed as deformable sheets or membranes, or manufactured into useful assay devices (e.g., microtiter dish (e.g., PVC, polypropylene, or polystyrene), a test tube (glass or plastic), a dipstick (e.g. glass, PVC, polypropylene, polystyrene, latex, and the like), a microcentrifuge tube) and the like. A preferred support is aminosilane, which will bind to negatively charged molecules. Another preferred support is layered silicates, a group of laminated silica minerals that include, but are not limited to: vermiculite, montmorillonite, bentonite, hectorite, fluorohectorite, hydroxyl hectorite, boron fluorophlogopite, hydroxyl boron phlogopite, mica, and the like. Preferred micas are those that can be fractured to produce a smooth surface, more preferably an atomically smooth surface.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like.

D) Binding of the First Component to the Support

As indicated above, in preferred solid phase assays either the test agent and/or a cytoskeletal component is attached to a solid support. The manner of linking a wide variety of compounds to various surfaces is well known and is amply illustrated in the literature (see, e.g., *Immobilized Enzymes*, Ichiro Chibata, Halsted Press, New York, 1978, and Cuatrecasas, (1970) *J. Biol. Chem.* 245 3059). Adhesion of a cytoskeletal component, and/or a test agent, to the solid support can be direct (i.e., the cytoskeletal component and/or test agent(s) directly contact the solid support) or indirect via a linker (i.e., the linker is a particular compound or compounds attached to the support, and the cytoskeletal component and/or test agent(s) bind to this compound or compounds rather than to the solid support).

Method of attaching biological, and other, molecules to solid supports are well known to those of skill in the art. For example, compounds have been immobilized either covalently (e.g., utilizing single reactive thiol groups of cysteine residues, Colliuod et al. (1993) *Bioconjugate Chem.* 4, 528-536)), or non-covalently but specifically (e.g., via immobilized antibodies (Schuhmann et al. (1991) *Adv. Mater.* 3: 388-391; Lu et al. (1995) *Anal. Chem.* 67: 83-87), the biotin/streptavidin system (Iwane et al. (1997) *Biophys. Biochem. Res. Comm.* 230: 76-80), metal-chelating Langmuir-Blodgett films (Ng et al. (1995) *Langmuir* 11: 4048-4055; Schmitt et al. (1996) *Angew. Chem. Int. Ed. Engl.* 35: 317-320; Frey et al. (1996) *Proc. Natl. Acad. Sci. USA* 93:4937-4941; Kubalek et al. (1994) *J. Struct. Biol.* 113: 117-123) and metal-chelating self-assembled monolayers (Sigal et al. (1996) *Analytical Chem.*, 68: 490-497) for binding of polyhistidine fusion proteins.

By manipulating the solid support and the mode of attachment of the cytoskeletal component to the support, it is possible to control the orientation of the cytoskeletal component. For example, copending patent application entitled "Reversible Immobilization of Arginine-tagged Moieties on a Silicate Surface, U.S. Ser. No. 60/057,929, filed on Sep. 4, 1997, PCT/US98/18531 describes the use of an arginine tail to attach cytoskeletal proteins to a mica film.

Thus, for example, where it is desired to attach a myosin molecule to a surface in a manner that leaves the myosin tails free to interact with other molecules, a tag (e.g., polyarginine or polyglutamate, magnetic particle, etc.) may be added to the myosin molecule at a particular position in the myosin sequence (for example, near the myosin head such that, when the myosin molecule is attached to a surface (e.g., a silicate surface by means of an arginine tag, an iron-containing surface by means of a magnetic tag, a metal (e.g. IMAC reagent) by means of a histidine tag, etc.), the tail is free. One preferred site for the placement of such an attachment tag is on loop two of the myosin head, a flexible external loop at the actin binding domain. Other sites include the myosin carboxy terminus. Other cytoskeletal proteins, such as kinesin, may similarly be modified to add an arginine tag to external loops or carboxy or amino termini.

If polyglutamate is used, the tag minimally comprises 3-4, preferably 6-8, and more preferably 10-15 glutamate residues. Proteins tagged with a polyglutamate tail will preferably bind to a positively charged surface, preferably aminosilane. Similar to the arginine tag, the polyglutamate tag can be used to orient the tagged cytoskeletal component, as described above. It is also possible to purify polyglutamate-tagged molecules on regular anion exchange columns.

In one embodiment, the invention involves binding of polymer-interacting proteins to a surface coated with polymers. High adsorption of polymers is achieved by first shearing polymers to short sizes (e.g., about 1μ or less) and then adsorbing them onto surfaces coated with inactivated motor proteins that bind tightly to the polymer. A motor protein can be inactivated by mutating the "motor domain" such that hydrolysis of chemical energy to produce mechanical force can no longer occur. Nonspecific binding is minimized by subsequent absorption of carrier protein (e.g., bovine serum albumin).

In one embodiment, the polymer-interacting proteins are labeled (e.g., fluorescently labeled), either chemically or by genetic fusion to a fluorescent protein (e.g., GFP). The reverse assay is also possible in which the polymer-interacting protein is adsorbed onto the surface and a fluorescently-labeled polymer is employed. If a binding interaction occurs, fluorescent protein is depleted from the solution and accumulates on the surface. A quantitative readout of fluorescence on the surface is made, for example, by total internal reflection, which selectively excites fluorescent molecules on the surface and not in the solution.

E) Test Compositions

The materials and methods of this invention are particularly useful for analyzing the effects of biological molecules on cytoskeletal interactions. Compounds suitable of assay in the methods of this invention include, but are not limited to, proteins, glycoproteins, antibodies, saccharides, lipids, nucleotides, nucleotide analogues, nucleic acids (e.g., DNA, RNA, peptide nucleic acids, etc.), and organic molecules, particularly small organic molecules.

Candidate agents encompass numerous chemical classes, though typically they are organic molecules, preferably small organic compounds having a molecular weight of more than 100 and less than about 2,500 daltons. Candidate agents preferably comprise functional groups suitable for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In an embodiment provided herein, the candidate bioactive agents are proteins. The protein may be made up of naturally occurring amino acids and peptide bonds, or synthetic peptidomimetic structures. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In another embodiment, the candidate bioactive agents are naturally occurring proteins or fragments of naturally occurring proteins. Thus, for example, cellular extracts containing proteins, or random or directed digests of proteinaceous cellular extracts, may be used. In one embodiment, the libraries are of bacterial, fungal, viral, and mammalian proteins, with the latter being preferred, and human proteins being especially preferred.

In one embodiment, the candidate agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In another embodiment, the candidate agents are nucleic acids. By "nucleic acid" or "oligonucleotide" or grammatical equivalents herein means at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) Tetrahedron 49(10):1925) and references therein; Letsinger (1970) J. Org. Chem. 35:3800; Sprinzl et al. (1977) Eur. J. Biochem. 81: 579; Letsinger et al. (1986) Nucl. Acids Res. 14: 3487; Sawai et al. (1984) Chem. Lett. 805, Letsinger et al. (1988) J. Am. Chem. Soc. 110: 4470; and Pauwels et al. (1986) Chemica Scripta 26: 141 9), phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321, O-methylphophoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31: 1008; Nielsen (1993) Nature, 365: 566; Carlsson et al. (1996) Nature 380: 207). Other analog nucleic acids include those with positive backbones (Denpcy et al. (1995) Proc. Natl. Acad. Sci. USA 92: 6097; non-ionic backbones (U.S. Pat. Nos. 5,386,023, 5,637,684, 5,602,240, 5,216,141 and 4,469,863; Angew. (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994), Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), Chem. Soc. Rev. pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine, hypoxanthine, isocytosine, isoguanine, etc.

As described above generally for proteins, nucleic acid candidate agents may be naturally occurring nucleic acids, random nucleic acids, or "biased" random nucleic acids. For example, digests of prokaryotic or eukaryotic genomes may be used as is outlined above for proteins.

In a preferred embodiment, the candidate bioactive agents are organic chemical moieties, a wide variety of which are available in the literature.

In a preferred embodiment, the candidate agent is a small molecule. The small molecule is preferably 4 kilodaltons (kd) or less. In another embodiment, the compound is less than 3 kd, 2 kd or 1 kd. In another embodiment the compound is less than 800 daltons (D), 500 D, 300 D or 200 D. Alternatively, the small molecule is about 75 D to 100 D, or alternatively, 100 D to about 200 D.

As indicated above, the test composition(s) can be provided as members of a "library" or "collection" of compounds. Such collections or libraries can be produces simply by combining two or more different test compositions. However for effective screening of a wide number of a wide number of different test compositions preferred libraries contain a large number of different compositions. Thus, library production often utilizes combinatorial chemical synthesis techniques to produce a "combinatorial chemical library". A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks (Gallop et al. (1994) 37(9): 1233-1250).

Such chemical libraries exist in a continuum between two functional objectives. "Broad screening" libraries are used to rapidly screen a wide range of diverse agents. Thus "broad screening" libraries are characterized by large library size, broad structural diversity, no specific structural goal and are typically synthesized utilizing a wide number of different "building blocks." At the other end of the spectrum, libraries are used for "chemical analoging" to provide subjects for screening a wide variety of related chemical analogues. Chemical analoging libraries are typically of moderate library size, show relatively narrow structural diversity, contain a relatively limited repertoire of building blocks are typically synthesized using a specific order of combination of building blocks.

Preparation and screening of combinatorial chemical libraries is well known to those of skill in the art (see, e.g., Gorden and Kerwin (1998) Combinatorial Chemistry and Molecular Diversity in Drug Discovery, John Wiley & Sons, Inc. N.Y.). Such combinatorial chemical libraries include, but are not limited to, peptide libraries (see, e.g., U.S. Pat. No. 5,010,175, Furka (1991) Int. J. Pept. Prot. Res., 37: 487-493, Houghton et al. (1991) Nature, 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al. (1993) *Proc. Nat. Acad. Sci. USA* 90: 6909-6913), vinylogous polypeptides (Hagihara et al. (1992) *J. Amer. Chem. Soc.* 114: 6568), nonpeptidal peptidomimetics with a β-D-Glucose scaffolding (Hirschmann et al., (1992) *J. Amer. Chem. Soc.* 114: 9217-9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658; Gordon et al., (1994) *J. Med. Chem.* 37: 1385), nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology*, 14(3): 309-314), and PCT/US96/10287), carbohydrate libraries (see, e.g., Liang et al. (1996) *Science,* 274: 1520-1522, and U.S. Pat. No. 5,593,853), and small organic molecule libraries (see, e.g., benzodiazepines: Baum (1993) *C&EN*, January 18, page 33; isoprenoids: U.S. Pat. No. 5,569,588; thiazolidinones and metathiazanones: U.S. Pat. No. 5,549,974; pyrrolidines: U.S. Pat. Nos. 5,525,735 and 5,519,134; morpholino compounds: U.S. Pat. No. 5,506,337; benzodiazepines: U.S. Pat. No. 5,288,514; and the like).

Devices for the preparation of combinatorial libraries are commercially available (see, e.g., 357 MPS, 390 NWS, Advanced Chem Tech, Louisville Ky.; Symphony, Rainin, Woburn, Mass.; 433A Applied Biosystems, Foster City, Calif.; 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate 11, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tfipos, Inc., St. Louis, Mo., ChemStar, Ltd, Moscow, RU, 3D Pharmaceuticals, Exton, Pa., Martek Biosciences, Columbia, Md., etc.).

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

III. Antibodies, Antisera, and Immunoassays

In certain circumstances, it may be necessary to detect the presence and concentration of certain compounds in solutions and in complex mixtures before performing the binding assays described above. One way of doing so is by the use of electrophoresis. A second way is to obtain polyclonal and monoclonal antibodies using methods known to those of skill in the art, and perform immunoassays (see, e.g., Coligan (1991), *Current Protocols in Immunology*, Wiley/Greene, NY; and Harlow and Lane (1989), *Antibodies: A Laboratory Manual*, Cold Spring Harbor Press, NY; Stites et al. (eds.) *Basic and Clinical Immunology* (4th ed.) Lange Medical Publications, Los Altos, Calif., and references cited therein; Goding (1986), *Monoclonal Antibodies: Principles and Practice* (2d ed.) Academic Press, New York, N.Y.; and Kohler and Milstein (1975) *Nature,* 256:495-497).

Such techniques include antibody preparation by selection of antibodies from libraries of recombinant antibodies in phage or similar vectors (see, Huse et al. (1989), *Science,* 246:1275-1281; and Ward et al. (1989), *Nature,* 341:544-546). For example, in order to produce antisera, a particular antigen a fragment thereof is isolated as described herein. For example, recombinant protein is produced in a transformed cell line. An inbred strain of mice or rabbits is immunized with the component using a standard adjuvant, such as Freund's adjuvant, and a standard immunization protocol. Alternatively, a synthetic peptide derived from the antigen and conjugated to a carrier protein can be used an immunogen. Polyclonal sera are collected and titered against the immunogen in an immunoassay. Polyclonal antisera with a titer of $10^4$ or greater are selected and tested for their cross reactivity against cytoskeletal components and test compositions or even other cytoskeletal components and test compositions, using a competitive binding immunoassay. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

A number of immunogens may be used to produce antibodies specifically reactive with either cytoskeletal components and test compositions. Recombinant protein is the preferred immunogen for the production of monoclonal or polyclonal antibodies. Naturally occurring protein may also be used either in pure or impure form. Synthetic peptides made using the cytoskeletal components and test compositions sequences described herein may also used as an immunogen for the production of antibodies to the protein. Recombinant protein can be expressed in eukaryotic or prokaryotic cells as described above, and purified as generally described above. The product is then injected into an animal capable of producing antibodies. Either monoclonal or polyclonal antibodies may be generated, for subsequent use in immunoassays to measure the cytoskeletal component.

Methods of production of polyclonal antibodies are known to those of skill in the art. In brief, an immunogen, preferably a purified cytoskeletal component, is mixed with an adjuvant and animals are immunized. The animal's immune response to the immunogen preparation is monitored by taking test bleeds and determining the titer of reactivity to the cytoskeletal components and test compositions. When appropriately high titers of antibody to the immunogen are obtained, blood is collected from the animal and antisera are prepared. Further fractionation of the antisera to enrich for antibodies reactive to the cytoskeletal component can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein (1976) *Eur. J. Immunol.* 6:511-519). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al. (1989) *Science* 246:1275-1281.

A particular antigen can be measured by a variety of immunoassay methods. For a review of immunological and immunoassay procedures in general, see *Basic and Clinical Immunology*, 7th Edition (D. Stites and A. Terr ed.) 1991. Moreover, immunoassays of the present invention can be performed in any of several configurations, which are reviewed extensively in *Enzyme Immunoassay*, E. T. Maggio, ed., CRC Press, Boca Raton, Fla. (1980); "Practice and Theory of Enzyme Immunoassays," P. Tijssen, *Laboratory Techniques in Biochemistry and Molecular Biology*, Elsevier Science Publishers B.V. Amsterdam (1985); and, Harlow and Lane, *Antibodies, A Laboratory Manual*, supra.

Immunoassays to cytoskeletal components and test agents of the present invention may use a polyclonal antiserum raised against the cytoskeletal component or test agent or a fragment thereof. This antiserum is selected to have low crossreactivity against other (non-cytoskeletal components and test compositions or cytoskeletal components and test compositions) proteins and any such crossreactivity is removed by immunoabsorption prior to use in the immunoassay.

In order to produce antisera for use in an immunoassay, the cytoskeletal component is isolated as described herein. For example, recombinant protein is produced in a transformed cell line. An inbred strain of mice such as balb/c is immunized with the selected cytoskeletal component using a standard adjuvant, such as Freund's adjuvant, and a standard mouse immunization protocol. Alternatively, a synthetic peptide derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-cytoskeletal components and test compositions, using a competitive binding immunoassay such as the one described in Harlow and Lane, supra, at pages 570-573.

Immunoassays in the competitive binding format can be used for the crossreactivity determinations. For example, the antigen can be immobilized to a solid support. Proteins (other cytoskeletal components and test compositions, or non-cytoskeletal components and test compositions) are added to the assay which compete with the binding of the antisera to the immobilized antigen. The ability of the above proteins to compete with the binding of the antisera to the immobilized protein is compared to the protein. The percent crossreactivity for the above proteins is calculated, using standard calculations. Those antisera with less than 10% crossreactivity with each of the proteins listed above are selected and pooled. The cross-reacting antibodies are optionally removed from the pooled antisera by immunoabsorption with the above-listed proteins.

The immunoabsorbed and pooled antisera are then used in a competitive binding immunoassay as described above to compare a second protein to the immunogen protein, either cytoskeletal components and test compositions. In order to make this comparison, the two proteins are each assayed at a wide range of concentrations and the amount of each protein required to inhibit 50% of the binding of the antisera to the immobilized protein is determined.

The presence of a desired polypeptide (including peptide, transcript, or enzymatic digestion product) in a sample may also be detected and quantified using Western blot analysis. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with labeling antibodies that specifically bind to the analyte protein. The labeling antibodies specifically bind to analyte on the solid support. These antibodies are directly labeled, or alternatively are subsequently detected using labeling agents such as antibodies (e.g., labeled sheep anti-mouse antibodies where the antibody to an analyte is a murine antibody) that specifically bind to the labeling antibody.

IV. Data Management.

In one embodiment, the assays of this invention are facilitated by the use of databases to record assay results. Particular with the use of large-scale screening systems, (e.g., screening of combinatorial libraries) data management can become a significant issue. For example, all natural hexapeptides have been synthesized in a single combinatorial experiment producing about 64 million different molecules. Maintenance and management of even a small fraction of the information obtained by screening such a library is aided by methods automated information retrieval, e.g. a computer database.

Such a database is useful for a variety of functions, including, but not limited to library registration, library or result display, library and/or result specification, documentation, and data retrieval and exploratory data analysis. The registration function of a database provides recordation/registration of combinatorial mixtures and assay results to protect proprietary information in a manner analogous to the registration/protection of tangible proprietary substances. Library and assay result display functions provide an effective means to review and/or categorize relevant assay data. Where the assays utilize complex combinatorial mixtures for test agents, the database is useful for library specification/description. The database also provides documentation of assay results and the ability to rapidly retrieve, correlate (or statistical analysis), and evaluate assay data.

Thus, in some preferred embodiments, the assays of this invention additionally involve entering test agent(s) identified as positive (i.e., having an effect on cytoskeletal activity) in a database of "positive" compounds and more preferably in a database of therapeutic or bioagricultural lead compounds.

The database can be any medium convenient for recording and retrieving information generated by the assays of this invention. Such databases include, but are not limited to manual recordation and indexing systems (e.g. file-card indexing systems). However, the databases are most useful when the data therein can be easily and rapidly retrieved and manipulated (e.g. sorted, classified, analyzed, and/or otherwise organized). Thus, in a preferred embodiment, the signature the databases of this invention are most preferably "automated", e.g., electronic (e.g. computer-based) databases. The database can be present on an individual "stand-alone" computer system, or a component of or distributed across multiple "nodes" (processors) on a distributed computer systems. Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

V. Kits.

In still another embodiment, this invention provides kits for practice of the assay methods described herein. The kits preferably comprise one or more containers containing one or more of the assay components described herein. Such components include, but are not limited to one or more cytoskeletal components, one or more test agent(s), solid supports (e.g., microtitre plates) with one or more attached components, buffers, labels, and other reagents as described herein.

The kits may optionally include instructional materials containing directions (i.e., protocols) for carrying out any of the assays described herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Observation of Kinesin Motor Binding to a Surface-Adsorbed Microtubule Detection by Total Internal Reflection Microscopy and Modulation of that Binding by Nucleotide To observe single motor molecule binding, motor-GFP fusions were prepared. Previous studies had shown that single GFP molecules (the Ser65Thr variant) can be detected by TIR microscopy (Pierce et al., 1997, *Nature* 388: 388). For the wild-type kinesin and the NK-1 chimera, GFP was fused C-terminal to residue 560. In the case of Ncd, GFP was fused N-terminal to residue 236, which retains ¾th of the Ncd coiled-coil stalk and the complete motor domain but lacks the N-terminal domain that bundles microtubules (Chandra et al. (1993) *J. Biol. Chem.* 268: 9005-9013.). This GFP fusion method is advantageous compared to fluorescent dye modification, which tends to inactivate the Ncd catalytic domain. Hydrodynamic and single fluorescent spot intensity analysis indicated that K560-GFP and Ncd-GFP are dimers under conditions of the assay.

By using green fluorescent protein fused to the polymer-binding protein, this assay can be performed in crude cell extracts. GFP chimeras provide two advantages. First, this alleviates the necessity of purifying the polymer-interacting protein to homogeneity before performing the binding assay. In many cases, purification and fluorescent labeling of many proteins is too difficult, due to their limited quantities in cells. Second, the drug screening effort can be performed in the protein environment of a whole cell extract. This is advantageous, since a complex mixture of competing molecules for the drug is present.

A) Expression Constructs

A human conventional kinesin construct comprising residues 1-560 with a C terminal 6 histidine (6xHis) tag was cloned into pET17B (Novagen, Inc.). The chimera NK-1 was constructed by performing PCR on the GST-MC1 construct (Chandra et al., 1993, *J. Biol. Chem.* 268: 9005-9013) with the 5' oligo corresponding to a.a. 348-359 and the 3' oligo corresponding to a.a. 656-667 to generate PCR product 1 (encoding a.a. 348-667). A second PCR reaction was performed on the K560-6xHis vector above using a 5' oligo corresponding to a.a. 323-333 and a 3' oligo corresponding to a.a. 7 and extending 14 b.p. into the vector promoter to generate a 3.9 kb product (PCR product 2) which included N- and C-terminal kinesin sequences as well as the intervening vector sequence. Products 1 and 2 were treated with alkaline phosphatase and the Klenow polymerase fragment to ensure blunt ends. The two PCR products were then ligated and transformed in DH5α cells. The C-terminal junction of the ligated product had a base pair deletion which was later repaired by PCR mutagenesis. The repaired chimera was then subcloned between Nde1 (a.a. 1) and Mun1 (a.a. 407) sites into the K560-6xHis pET17B vector in order to eliminate any PCR-induced errors in the vector. NK-2 was generated by the same strategy as indicated above with the exception that the 5' oligo for PCR product I corresponded to a.a. 49-60 and the 3' oligonucleotide for PCR product 2 corresponded to a.a. 48-37. The NK-3 construct was generated by Stratagene QuikChange protocol (Stratagene, Inc.) using oligonucleotides that substituted the Ncd L11 sequence (a.a. 586-597) for the kinesin L11 sequence (a.a. 237-252) in the K560-6xHis pET17B vector. The remainder of the cloning was as described in Woehlke et al. (1997), *Cell* 90: 207-216. All coding regions were confirmed by DNA sequencing.

For GFP fusion proteins (see FIG. 1), PCR was used to introduce: 1) a 5' Nde1 site and a 3' Kpn1 site at a.a. 560 of human ubiquitous kinesin and NK-1, and 2) a 5' Kpn1 site and a 3' 6xHis tag plus an Xho1 site to GFP mutant S65T (from R. Tsien (UCSD)). K560 and NK-1 were then fused to GFP at the introduced Kpn1 site (which adds a Gly-Thr linker sequence) and cloned into pET17b between the Nde1 and Xho1 sites. To make the Ncd-GFP fusion, a 5' Kpn1 site and a 3' Xho1 site were added to Ncd a.a. 236-700, and a 5' Nhe1 site plus 6xHis tag and 3' Kpn1 site were added to GFP (again adding a Gly-Thr linker sequence) via PCR. These products were joined together into the Nhe1-Xho1 sites of pET17b. All PCR-derived sequences were confirmed by DNA sequencing.

B) Bacterial Protein Expression

Constructs were transformed into *E. coli* strain BL21 (DE3), grown in TPM-ampicillin (20 g/l tryptone, 15 g/l yeast extract, 8 g/l NaCl, 10 mM glucose, 2 g/l $Na_2HPO_4$, 1 g/l $KH_2PO_4$, and 100 μg/ml ampicillin) at 24° C. to an $O.D._{600}$ of 1-2, and then protein expression was induced for 9-14 hr with 0.2 mM IPTG. Cells were lysed by French press (0.8 MPa) in 50 mM $NaPO_4$, 20 mM imidazole, 250 mM NaCl, 1 mM $MgCl_2$, 0.5 mM ATP, 10 mM P-mercaptoethanol (βME), leupeptin (1 μg/ml), pepstatin (1 μg/ml), chymostatin (1 μg/ml), aprotinin (1 μg/ml), and 0.25 mg/ml Pefabloc (Boehringer Mannheim)(50 ml buffer per 2 l culture). The supernatant from a 28,000×g, 30 min centrifugation was collected and incubated with Ni—NTA resin (Qiagen, Inc.) for 1 hr at 4° C. (1-2.5 ml resin per 50 ml of supernatant). The mixture was then transferred to a disposable column, and the resin was washed with 50 ml of 50 mM $NaPO_4$ (pH 6), 250 mM NaCl, 1 mM $MgCl_2$, 0.1 mM ATP, and 10 mM βME. Proteins were eluted with 50 mM $NaPO_4$, 500 mM imidazole-Cl, 250 NaCl, 1 mM $MgCl_2$, 0.1 mM ATP, and 10 mM βME (pH 7.2). The peak fractions were then diluted 5-fold into column buffer supplemented with 50 mM NaCl and further purified by mono-Q chromatography.

The K560-GFP and NK-1-GFP fusion proteins were purified by mono-Q chromatography with elution at 0.35 M NaCl in a 16 ml 0.2-1.0 M gradient in 25 mM NaPipes (pH 6.8; K560-GFP) or 10 mM NaPO$_4$ (pH 7.2; NK-1-GFP) with 2 mM MgCl$_2$, 1 mM EGTA, 1 mM DTT, and 0.1 mM ATP. Ncd-GFP was further purified by mono-S chromatography with elution at 0.3 M NaCl in a 30 ml 0.1-1.1 mM NaCl gradient in 10 mM NaPO$_4$ (pH 7-2), 2 mM MgCl$_2$, 1 mM EGTA, 1 mM DTT, and 0.1 mM ATP. The motor-GFP fusion proteins were then subjected to an additional microtubule affinity purification step by incubating with microtubules and 1 mM AMPPNP, centrifuging the motor-microtubule complex and releasing the active motor from the microtubule with 5 mM MgATP/200 mM KCl.

For all preparations, 10-20% sucrose was added to peak fractions before freezing and storage in liquid nitrogen. Protein concentrations were calculated by running the kinesin along with a BSA-standard curve on a SDS polyacrylamide gel, staining with Coomassie, capturing the gel image with a ccd camera, and then measuring optical densities using the computer program NIH Image.

Motors from the peak mono-Q fractions were adsorbed onto glass surfaces of microscope flow cells at concentrations of 0.5-10 µM. For motor-GFP fusion proteins, affinity-purified anti-GFP polyclonal antibodies (0.5 mg/ml) were first adsorbed onto the glass surface, the flow cell was washed with buffer, and the motors were then allowed to bind to the antibody-coated surface. A buffer containing 15 mM NaMOPS (pH 7), 50 mM NaCl, 20 µM taxol, 10 µg/ml rhodamine-labeled microtubules (Hyman et al., 1990, *Meth. Enzym.* 196: 303-319.), 1 mM ATP, 1 mM EGTA, 2 mM MgCl$_2$, 1 mM DTT, 2 mg/ml casein, and an oxygen depletion system composed of 22 mM glucose, 0.5% P-mercaptoethanol, 0.2 mg/ml glucose oxidase, and 36 µg/ml catalase (Harada et al., 1990, *J. Mol. Biol.* 216: 49-68.). Binding was also observed in the lower ionic strength buffers employed in the single molecule fluorescence motility assays.

Polarity marked microtubules (Hyman (1991) *J. Cell Sci. Supp.* 14: 125-127) were prepared by first polymerizing short microtubules from rhodamine-tubulin and 0.5 mM GMPCPP (a nonhydrolyzable GTP analog)—These brightly labeled microtubules were then used as seeds to polymerize a more dimly labeled microtubule segment with 0.1 mg/ml rhodamine-labeled tubulin, 1.5 mg/ml unlabeled tubulin, and 1.5 mg/ml NEM-modified tubulin (Hyman et al., 1990, *Meth. Enzym.* 196: 303-319.) which inhibits minus-end growth. Polarity marked microtubules were used.

For the single molecule fluorescence assay, motor-GFP proteins were diluted to a concentration of 1-50 nM in a buffer containing 1 mM ATP, 1 mM EGTA, 2 mM MgCl$_2$, 7.5 mg/ml bovine serum albumin (BSA) as carrier protein, and the oxygen depletion system described above. Kinesin-GFP was standardly assayed in the above solution with 12 mM KPipes (pH 6.8). A variety of buffer conditions were also used, including 12 mM KPipes (pH 6.8), 12 mM KMOPS (pH 7), 50 mM KMOPS (pH 7), and 50 mM KMOPS (pH 7) with 50 mM NaCl.

C) Microscopy and Analysis

Rhodamine-labeled microtubules were illuminated with a 100 W mercury lamp and imaged by epifluorescence microscopy using a 60×, 1.4 N.A. objective (Olympus, Inc). The image was projected onto a silicon-intensified target camera (Hamamatsu, Inc.) and then recorded onto SVHS tape.

For single molecule fluorescence imaging, 4 µl of assay mix described above was spotted onto a cleaned quartz slide, covered with an 18 mm coverslip, sealed with rubber cement, and imaged on a low-background TIR optical bench microscope constructed by the authors (Pierce and Vale, 1997). Briefly, an argon-ion laser was used at 488 nm and 5 mW to excite GFP, and a HeNe laser was operated at 0.4 mW to excite sea urchin axonemes (prepared as described by Gibbons and Fronk (1979), *J. Biol. Chem.* 254: 187-196) and labeled with Cy5 dye (Vale et al., 1996, *Nature* 380, 451-453). Laser illumination was passed through a X/4 plate set to produce circularly polarized light and focused by 25 cm lens at an appropriate angle through a prism to produce total internal reflection and evanescent field illumination of a ~30×40 mm area at the sample (Funatsu et al., 1995, *Nature* 374: 555-559). Fluorescence was collected by a Nikon PlanApo 100/1.4 objective, collimated, passed through custom designed dichroic mirror and barrier filters and focused onto a CCD camera coupled to a selected SR UB Gen3+ intensifier tube from Stanford Photonics Inc. Data was recorded to video tape after contrast enhancement by an Argus-20 image processor (Hamamatsu Photonics, Inc.). Behavior of single GFP molecule fluorescence is described elsewhere (Pierce et al., 1997, *Nature* 388: 388).

When K560-GFP was combined with axonemal microtubules and ATP, individual fluorescent spots could be easily observed binding to the axoneme, as shown previously (Pierce et al., 1997, *Nature* 388: 388). In contrast, at 10 nM NK-1-GFP and Ncd-GFP, fluorescent spots did not associate with axonemes at more than background levels, indicating that microtubule associations must be very transient. The capacity of Ncd-GFP and NK-1-GFP to bind to microtubules in this assay was demonstrated by inducing a strong microtubule binding state by depleting ATP, which resulted in the association of the majority of fluorescent molecules with the axoneme The above method involves selective surface illumination and viewing without removing free protein in solution. However, using an extra step of physically removing the solution, a fluorescence reading of the surface can be made using a conventional fluorimeter.

Example 2

Reversible, Site-Specific Immobilization of Arginine-Tagged Fusion Proteins on Mica Surfaces This example describes the specific binding of polyarginine tagged proteins to atomically flat negatively charged mica surfaces. The polyarginine tags were expressed as fusion proteins. It is shown herein that the arginine (e.g., hexaarginine) tagged proteins bind to mica via the Arg-tag based on ion exchange of naturally occurring potassium cations. Only nonspecific binding was observed with the control protein that is free of the Arg-tag. This novel technology facilitates the uniform and specific orientation of immobilized proteins on a standard substrate used for many surface-related applications.

A) Materials and Methods

Muscovite mica was obtained from Provac (Liechtenstein). The plasmid pGFPuv was from Clontech (Palo Alto, Calif.) and the vector pET28a(+) was from Novagen (Madison, Wis.). All other reagents were from Sigma Chemical (St. Louis, Mo.) and of highest available grade. Ultrapure water with a resistance of 18 Nffcm was used for all aqueous buffers (purified by passage through a Mlli-Q purification system).

B) Preparation of GFPH6, GFPH6R6, GFPR6

For the addition of six histidine residues to the N-terminus of GFP, two oligodeoxyribonucleotide primers were designed: one corresponding to the N-terminal part of the GFP gene (5'-GGA ATT CCA TAT GAG TAA AGG AGA AGA ACT TTT C-3', designated primer #1, SEQ ID No: 1) and a second corresponding to the C-terminal part (5'-GAC CGG CGC TCA GTT GGA ATT C-3', designated primer #2, SEQ ID No: 2). These oligodeoxyribonucleotides were used for PCR with 20 ng of linearized pGFPuv as template. The amplified fragments, digested with Nde1 and BamH1, were ligated with the linearized expression vector pET28a(+). The resulting plasmid pGFPH6 was used for transformation of *E. coli* BL21(DE3). Standard protocols were followed for DNA handling and bacterial transformation (Sambrook et al. (1989) *Molecular Cloning: A Laboratory Manual*, Cold Spring Harbor: Cold Spring Harbor Laboratory Press).

To introduce a tag of six arginine residues on either the N- or C-terminal part of GFP, the same procedure was used with the following oligodeoxyribonucleotides: (primer #2) and 5'-GGA ATT CCA TAT GCG CCG TCG CCG TCG CCG TAT GAG TAA AGG AGA AGA ACT TTT C-3' for GFPH6R6, (primer #1) and 5'-TTG GAA TTC ATT AGC GAC GGC GAC GGC GAC GCG CGG TGC CTT TGT AGA GCT CAT CCA TG-3' for GFPR6. The PCR and cloning procedure was performed as described above. The resulting plasmids pGFPH6R6 and pGFPR6 were used to transform *E. coli* BL21(DE3).

C) Expression and Purification of the Recombinant Proteins

All of the expressed proteins carry a vector-encoded tag of a hexa-histidine sequence for purification by metal chelate affinity chromatography on a $Ni^{2+}$/NTA matrix (Qiagen, Santa Clarita, Calif.). The cells were grown at 37° C. by shaking in LB-medium containing 25 mg/ml Kanamycin. At an $OD_{600}$ of 0.8 the cells were induced with 1 mM IPTG, and 5 h later, they were harvested by centrifugation at 6000×g for 10 min. The cells were lysed by addition of lysozyme at a concentration of 100 mg/ml and 10% (v/v) of 1% Triton X-100 in 50 mM Tris-HCl pH 7.5, 50 mM KCl, 1 mM EDTA. After incubation for 30 min on ice, $MgCl_2$ was added to a final concentration of 40 mM. The liberated DNA was digested by adding 0.2 mg DNaseI per ml lysate. The lysate was incubated for 15 min on ice and then centrifuged at 30,000×g for 40 min. The clear supernatant was dialyzed against buffer containing 10 mM Hepes/NaOH pH 7.4, 50 mM NaCl, and then applied to a $Ni^{2+}$/NTA column. Weakly bound proteins were eluted with 10 mM imidazole pH 8.0. The his-tagged proteins were eluted with 500 mM imidazole in the case of the GFPH6 and with 500 mM imidazole, 500 mM NaCl for all the other variants (the Arg-tag caused a strong ionic interaction with the $Ni^{2+}$/NTA matrix). The eluted proteins were dialyzed against buffer containing 10 mM Hepes/NaOH pH 7.4, 50 mM NaCl, 50% glycerol and stored at −20° C. The purity of the recombinant proteins was estimated by SDS-polyacrylamide gel electrophoresis and found to be greater than 95%.

D) Protein Adsorption to Mica

Mica sheets were cut into pieces of 5×5 cm and freshly cleaved immediately before use. Droplets of protein solutions (GFPH6, GFPR6, GFPH6R6) at a concentration of 10 mg/ml were applied onto the previously unexposed, hydrophilic surfaces resulting in 2 aqueous films of approximately 4 $cm^2$ in size. After incubation for 5 min, the mica sheets were washed with 10 ml of water. The central parts, 1 $cm^2$ in size, were then cut out to ensure that no contaminants from the edges could falsify the subsequent analyses. For each data point four surfaces were analyzed and the readings were averaged. These surfaces, stored separately in Eppendorf tubes, were then subjected to consecutive one-min washing steps with 400 ml 10 mM Hepes/NaOH buffer pH 7.4 containing increasing concentrations of salt with different mono- and bivalent cations (50, 125, 250 mM, $Na^+$, $K^+$, $Mg^{2+}$). For quantitation of active, adsorbed GFP, the eluates were collected separately and analyzed by fluorescence measurement at 509 nm (excitation at 395 nm) using an SLM8000 spectrophotometer (Aminco, Silver Spring, Md.) and GFP of known concentration as standard.

Qualitative determination of immobilized GFP was carried out with X-ray photoelectron spectroscopy (XPS) using the N1s narrow scans normalized against the corresponding Si2s peaks, an element that does not occur in proteins. For this purpose the adsorbed proteins were washed with the same salt-containing solutions as mentioned above (without buffer) and finally rinsed with ultrapure water and dried under a stream of nitrogen. This ensured that the XPS spectra were not dominated by crystallized salts.

D) X-Ray Photoelectron Spectroscopy (XPS)

XPS was carried out on a Surface Science Model 150 XPS spectrometer with an AlKα source (1486 eV), a quartz monochromator, hemispherical analyzer, and a multichannel detector. A nickel grid, directly positioned above the samples, and a charge neutralizer were used to prevent artifacts due to charging effects. The spectra were accumulated at a take-off angle of 35" and an angular acceptance of 30", with a 250×1000 μm spot size at a pressure of less than $1×10^{-8}$ Torr. The N1s peaks shown in this example were normalized against Si2s and corrected for the number of scans and the atomic sensitivity factors.

The results show that only about 1 pmol of the Arg-tag free GFPH6 remained bound after extensive washing with 10 mM Hepes/NaOH, pH 7.4. In contrast about 3 pmol of Arg-tagged GFP remained bound after this wash. Essentially all of the Arg-tag free GFPH6 was removed from the surface by consecutive washing steps with increasing concentrations of NaCl. In contrast, only about 50% of the two GFP variants comprising hexaarginine-tags (GFPR6H6 and GFPR6) came off with NaCl. The complete release could be achieved by elution with arginine-containing wash buffer. It is likely that this arginine-releasable protein was exclusively bound via its Arg-tag, whereas that released in the NaCl washing steps stemmed primarily from protein electrostatically bound to the surface via other charged groups in the protein.

Example 3

Solution-Phase Assays: Use of ATPase Assays in Screening Microtubule Binding Agents A) Preparation of Sponge Extract for Screening.

The sponge *Adocia* (*Haliclona*) sp. (Collection #95-100) was collected in Palau, Western Caroline Islands, and was quickly frozen. The frozen sponge (225 g) was diced and steeped in a mixture of dichloromethane (300 mL) and methanol (1 L) for 24 h. The solids were removed by filtration and the solution was reduced in volume to 300 mL and extracted with dichloromethane (2×200 mL).

The aqueous phase was lyophilized to yield a pale yellow powder. The powder (1.0 g) was chromatographed twice on a reversed phase C18 Sep-Pak, using a gradient of 30% MeOH in $H_2O$ to 100% methanol (MeOH) as eluant, to obtain pure fractions containing adociasulfate-1 and adociasulfate-2 and a mixed fraction containing adociasulfates. The mixed fraction was separated by reversed phase HPLC using 1:1 MeOH—$H_2O$ as eluant. Pure fractions were combined to obtain adociasulfate-1 (13.5 mg), adociasulfate-2 (14.1 mg) and adociasulfate-3 (3.3 mg).

B) Motility Assay.

TI-γ (a kinesin superfamily member from the fungus *Thermomyces lanuginosus*) was adsorbed to a glass coverslip and supplemented with a mixture of microtubules, 2 mM Mg-ATP, and sponge extracts in DMSO (5% final concentration). Motility was scored visually on a Zeiss Axioplan microscope sat up for DIC and fitted with an Argus 10 video processor (Hamamatsu).

C) Proteins.

All kinetic and binding measurements were performed on a bacterially expressed *Drosophila* kinesin heavy chain fragment containing amino acids 5-351 of the wild type protein and a hexahistidine tag at the C-terminus. Protein was purified from the soluble fraction of IPTG induced bacterial cells by a single round of affinity chromatography on Ni—NTA-agarose (Qiagen), concentrated by microfiltration, and frozen in small aliquots in liquid nitrogen.

D) Steady State Kinetics.

Initial rate measurements were done at room temperature using a malachite green assay (Geladopoulos et al. (1991) *Anal. Biochem.*, 192: 112-116) modified to work in 96 well microtiter plates and scored on a plate reader at 650 nm. ATP concentration dependence and basal ATPase rate were determined by a coupled enzymatic assay with pyruvate kinase and lactate dehydrogenase monitoring changes in absorbance at 340 nm. Phosphate standards (650 μM-7 μM) were included with each reading.

E) ATPase Assay (ADP Release).

The percent of ADP released from the enzyme was determined by the methods of Hackney (see, e.g., Hackney (1994) *J. Biol. Chem.*, 2690: 16508-16511). Briefly, 80 μM kinesin was preincubated with α-$^{32}$PATP at room temperature for 15 min and than stored on ice. 1 μl aliquots of that mixture were diluted into 100 μl of "chase mix" containing 0.5 mg/ml pyruvate kinase, 2 mM phosphoenalpyruvate, and varying concentrations of adociasulfate. At different time points 5 μl aliquots of the chase mix were quenched in 100 μl 1 M HCV/1 mM ATP/1 mM ADP. The amount of ADP that became accessible to pyruvate kinase and was converted to ATP was determined by a thin layer chromatography on PEI-cellulose followed by phosphoimager quantitation.

F) Results

Extracts from 268 marine sponges were initially tested for their ability to disrupt normal behavior of microtubules in a gliding motility assay. This screening method allowed immediate distinction between substances that affected microtubule movement and those that caused microtubule depolymerization or breakage. Active extracts from the initial screening were then tested for inhibition of the microtubule-stimulated kinesin ATPase.

The most promising candidates were extracts from the sponge *Adocia* sp. In the motility assay, these extracts disrupted microtubule attachment to the kinesin-coated surface, and totally abolished movement. The microtubule stimulated ATPase of kinesin was also completely inhibited.

Three active compounds in the extract were identified and isolated. These specific compounds are referred to herein as adociasulfates while the generic compounds are referred to as *Adocia* compounds or *Adocia* kinesin inhibitors. The structure of the *Adocia* compounds or adociasulfates does not resemble that of nucleotide triphosphates. This indicates that the *Adocia* structures are different from known kinesin inhibitors. In addition, it is believed that the activity spectrum of the *Adocia* compounds is narrower than that of nucleotide triphosphates or analogues thereof.

To further investigate specificity, one adociasulfate was tested on a variety of ATPases using the ATPase activity assay described above. Of those tested, the only enzymes substantially inhibited by adociasulfate are members of kinesin superfamily (Table 2).

TABLE 2

Concentrations of adociasulfate causing 50% inhibition of enzymatic activity.

| enzyme | C50 |
| --- | --- |
| rabbit kidney ATPase | >136 μM* |
| Apyrase | >136 μM* |
| Myosin II (EDTA)$^A$ | 75 μM |
| CENP-E | 10 μM$^D$ |
| K5-351$^B$ | 2 μM$^E$ |
| K411$^C$ | 2 μM$^E$ |
| TI-γ | 2 μM$^E$ |
| ncd | — |
| myosin | — |
| pyruvate kinase | — |

*enzyme was not inhibited by 50% at the highest used inhibitor concentration of 136 μM.;
$^A$EDTA activated ATPase;
$^B$construct containing amino acids 5–351 of *Drosophila* kinesin;
$^C$construct containing first 411 amino acids of *Drosophila* kinesin;
$^D$at 6 μM tubulin;
$^E$at 2 μM tubulin The behavior observed in the motility assay indicated that adociasulfates interfere with microtubule binding to the motor. This was tested by performing a kinesin-microtubule co-sedimentation assay in the presence of a nonhydrolysable ATP analog, AMP-PNP, with or without adociasulfate. Addition of adociasulfate abolished binding of kinesin to microtubules under these conditions.

Consideration of the kinesin mechanochemlcal cycle suggests that the effect on microtubule binding could be induced either by looking the kinesin in a weakly-binding state resembling the kinesin-ADP intermediate by adociasulfate binding in the nucleotide pocket, or by direct interference with the microtubule-binding site. Steady state kinetic measurements demonstrated that the adociasulfate-induced inhibition is competitive with microtubules, and could be totally reversed by high microtubule concentrations.

In contrast, varying the ATP concentration had no effect on the overall shape of the kinetic curves. $V_{max}$ was progressively lower at higher adociasulfate concentrations. An additional argument against adociasulfate binding at the nucleotide pocket comes from the lack of an inhibitory effect on the basal, non microtubule-stimulated rate of the kinesin ATPases. If adociasulfate interfered with nucleotide binding, or locked the enzyme in a particular nucleotide-bound state, ATP turnover in the absence of microtubule should be decreased. However, concentrations of up to 136 μM adociasulfate (the highest tested) did not inhibit the basal ATPase rate.

Microtubule binding to kinesin induced 1,000-fold stimulation of the basal ATPase rate, owing primarily to accelerated ADP release. It was tested whether adociasulfate binding to kinesin could mimic the effect of the microtubule by examining ADP release from kinesin in the presence of varying concentrations of adociasulfate. Indeed, bursts of ADP release were observed and their magnitude correlated positively with the concentration of adociasulfate. The adociasulfate concentration at 50% of maximum burst is much higher than the $K_1$ determined in steady state microtubule competition assays. This discrepancy may reflect different affinities for adociasulfate in different nucleotide states of kinesin. Steady state kinetic measurements of $K_1$ reflect the affinity of the most tightly bound state of the entire cycle, which includes several kinesin-nucleotide intermediates (K-ATP, K-ADP-Pi, K-ADP etc.).

In contrast, the ADP release experiment with adociasulfate involved only one state, K-ADP. It is intriguing that this state also has the lowest affinity for the microtubule. It was initially surprising that adociasulfate did not stimulate the kinesin basal ATPase even though it induced ADP release. However, during steady state kinetic measurements, each single headed kinesin molecule must undergo several cycles of attachment-detachment to microtubule subunits. In contrast, AS presumably remains bound through multiple enzymatic turnovers. The physiological equivalent of such a state would be a kinesin molecule permanently attached to a single tubulin dimer, a state for which no kinetic data exist. However, if the adociasulfate binding to kinesin resembles microtubule binding, the initial association event should result in a burst of ADP release as observed.

Although the foregoing invention has been described in some detail by way of illustration and example for purposes of clarity of understanding, it will be obvious that certain changes and modifications may be practiced within the scope of the appended claims. All publications, patents and patent applications mentioned in this specification are hereby incorporated by reference in their entirety for all purposes, to the same extent as if each individual publication, patent or patent application had been specifically and individually indicated to be incorporated by reference.

What is claimed is:

1. A method of identifying a therapeutic lead compound that modulates activity of a cytoskeletal system, said method comprising:

i) providing an assay mixture comprising a first component of said cytoskeletal system and a second component of said cytoskeletal system, wherein said cytoskeletal system is a microtubule system, and wherein said first component comprises a kinesin motor protein and said second component comprises a tubulin protein that specifically bind to each other;

ii) contacting said assay mixture with a test compound to be screened for the ability to inhibit or enhance binding between said first component and said second component;

iii) detecting a change in coupling between ATP hydrolysis and force generation; wherein said change indicates that said test compound modulates activity said cytoskeletal system.

2. The method of claim 1, further comprising step iv) testing said test compound on a variety of ATPases.

3. The method of claim 1, wherein said assay mixture comprises a cell lysate.

4. The method of claim 1, wherein at least 50 test compounds are screened.

5. The method of claim 2, wherein said variety of ATPases comprises CENP-E.

6. The method of claim 2, wherein said variety of ATPases comprises kinesin.

7. The method of claim 2, wherein said variety of ATPases comprises TI-gamma.

* * * * *

UNITED STATES PATENT AND TRADEMARK OFFICE
CERTIFICATE OF CORRECTION

PATENT NO. : 7,252,950 B1  Page 1 of 1
APPLICATION NO. : 10/031819
DATED : August 7, 2007
INVENTOR(S) : Ronald Vale et al.

It is certified that error appears in the above-identified patent and that said Letters Patent is hereby corrected as shown below:

ON THE TITLE PAGE

Correct item (75) Inventors: to read as follows:

Ronald Vale, Tiburon, CA (US);
Daniel Pierce, Hayward, CA (US);
James Spudich, Palo Alto, CA (US);
Lawrence S. B. Goldstein, San Diego, CA (US)

Signed and Sealed this

Thirty-first Day of August, 2010

David J. Kappos
*Director of the United States Patent and Trademark Office*